(12) United States Patent
Li et al.

(10) Patent No.: US 12,245,871 B2
(45) Date of Patent: Mar. 11, 2025

(54) FLEXIBLE SENSOR DETECTION SYSTEM FOR MEDICAL CARE AND HEALTH

(71) Applicants: QINGDAO UNIVERSITY OF TECHNOLOGY, Shandong (CN); QINGDAO HUANGHAI UNIVERSITY, Shandong (CN); GUOHUA (QINGDAO) INTELLIGENT PRECISION DRIVE CONTROL TECHNOLOGY RESEARCH INSTITUTE CO., LTD., Shandong (CN); QINGDAO JIMO QINGLI INTELLIGENT MANUFACTURING INDUSTRY RESEARCH INSTITUTE, Shandong (CN)

(72) Inventors: Changhe Li, Shandong (CN); Xifeng Wu, Shandong (CN); Xin Cui, Shandong (CN); Yanbin Zhang, Shandong (CN); Liang Luo, Shandong (CN); Min Yang, Shandong (CN); Dongzhou Jia, Shandong (CN); Teng Gao, Shandong (CN); Mingzheng Liu, Shandong (CN); Shuai Chen, Shandong (CN); Wuxing Ma, Shandong (CN); Bingheng Lu, Shandong (CN); Yali Hou, Shandong (CN); Runze Li, Shandong (CN); Huajun Cao, Shandong (CN)

(73) Assignees: QINGDAO UNIVERSITY OF TECHNOLOGY, Shandong (CN); QINGDAO HUANGHAI UNIVERSITY, Shandong (CN); GUOHUA (QINGDAO) INTELLIGENT PRECISION DRIVE CONTROL TECHNOLOGY RESEARCH INSTITUTE CO., LTD., Shandong (CN); QINGDAO JIMI QINGLI INTELLIGENT MANUFACTURING INDUSTRY RESEARCH INSTITUTE, Shandong (CN)

(*) Notice: Subject to any disclaimer, the term of this patent is extended or adjusted under 35 U.S.C. 154(b) by 937 days.

(21) Appl. No.: 17/281,998
(22) PCT Filed: Feb. 6, 2020
(86) PCT No.: PCT/CN2020/074403
§ 371 (c)(1),
(2) Date: Apr. 1, 2021
(87) PCT Pub. No.: WO2021/134857
PCT Pub. Date: Jul. 8, 2021

(65) Prior Publication Data
US 2022/0142573 A1    May 12, 2022

(30) Foreign Application Priority Data
Dec. 31, 2019  (CN) .................. 201911413320.9

(51) Int. Cl.
*A61B 5/00* (2006.01)
*A61B 5/0205* (2006.01)
(Continued)

(52) U.S. Cl.
CPC .......... *A61B 5/6805* (2013.01); *A61B 5/0006* (2013.01); *A61B 5/0008* (2013.01);
(Continued)

(58) Field of Classification Search
CPC ... A61B 5/6805; A61B 5/0006; A61B 5/0008; A61B 5/0024; A61B 5/02055;
(Continued)

(56) References Cited
U.S. PATENT DOCUMENTS

| | | | |
|---|---|---|---|
| 2015/0102925 A1* | 4/2015 | Foldyna ................. | A61F 7/00 600/323 |
| 2015/0119677 A1* | 4/2015 | Liu ...................... | A61B 5/28 600/389 |

(Continued)

FOREIGN PATENT DOCUMENTS

| | | |
|---|---|---|
| CN | 101073495 | 11/2007 |
| CN | 103445763 | 12/2013 |

(Continued)

OTHER PUBLICATIONS

"International Search Report (Form PCT/ISA/210) of PCT/CN2020/074403," mailed on Sep. 27, 2020, pp. 1-8.

*Primary Examiner* — Shirley X Jian
*Assistant Examiner* — Laura Hodge
(74) *Attorney, Agent, or Firm* — JCIPRNET

(57) ABSTRACT

The present invention discloses a flexible sensor detection system for medical care and health, including: an information collection module, which uses a wearable device as a carrier, where flexible sensors are respectively arranged on the wearable device; an information transmission module, configured to wirelessly transmit collected information to an information processing and feedback module; and the information processing and feedback module, configured to perform grading treatment on received data information and feed back a health condition corresponding to the data information to the information transmission module, where the information transmission module compares feedback health condition data with a preset health threshold to determine whether to give an alarm. A heart rate ECG band, a breathing band, a shell temperature band, a blood flow rate band, a blood glucose band, a blood oxygen band, and a deep temperature band of the present invention are provided with the built-in flexible sensors.

7 Claims, 10 Drawing Sheets

(51) Int. Cl.
| | |
|---|---|
| *A61B 5/024* | (2006.01) |
| *A61B 5/026* | (2006.01) |
| *A61B 5/08* | (2006.01) |
| *A61B 5/145* | (2006.01) |
| *A61B 5/318* | (2021.01) |
| *H01L 31/053* | (2014.01) |
| *H10N 10/13* | (2023.01) |
| *H10N 10/852* | (2023.01) |
| *H10N 30/045* | (2023.01) |
| *H10N 30/098* | (2023.01) |
| *H10N 30/30* | (2023.01) |
| *H10N 30/857* | (2023.01) |

(52) U.S. Cl.
CPC ........ *A61B 5/0024* (2013.01); *A61B 5/02055* (2013.01); *A61B 5/02438* (2013.01); *A61B 5/026* (2013.01); *A61B 5/0816* (2013.01); *A61B 5/14532* (2013.01); *A61B 5/14542* (2013.01); *A61B 5/318* (2021.01); *A61B 5/6803* (2013.01); *A61B 5/746* (2013.01); *H01L 31/053* (2014.12); *H10N 10/13* (2023.02); *H10N 10/852* (2023.02); *H10N 30/045* (2023.02); *H10N 30/098* (2023.02); *H10N 30/302* (2023.02); *H10N 30/857* (2023.02); *A61B 2560/0214* (2013.01); *A61B 2562/125* (2013.01); *A61B 2562/164* (2013.01)

(58) Field of Classification Search
CPC ... A61B 5/02438; A61B 5/026; A61B 5/0816; A61B 5/14532; A61B 5/14542; A61B 5/318; A61B 5/6803; A61B 5/746
See application file for complete search history.

(56) References Cited

U.S. PATENT DOCUMENTS

| | | | | |
|---|---|---|---|---|
| 2018/0325384 | A1* | 11/2018 | Agarwal | H10N 30/098 |
| 2019/0380646 | A1* | 12/2019 | Gertsch | A41D 1/002 |

FOREIGN PATENT DOCUMENTS

| | | | | |
|---|---|---|---|---|
| CN | 103445763 | A | * | 12/2013 |
| CN | 104257359 | | | 1/2015 |
| CN | 106039524 | | | 10/2016 |
| CN | 106501376 | | | 3/2017 |
| CN | 107356291 | | | 11/2017 |
| CN | 107951473 | | | 4/2018 |
| CN | 108670244 | A | * | 10/2018 |
| CN | 108871629 | | | 11/2018 |
| CN | 208490892 | U | * | 2/2019 |
| CN | 209332036 | U | * | 9/2019 |
| WO | 2019217828 | | | 11/2019 |

* cited by examiner

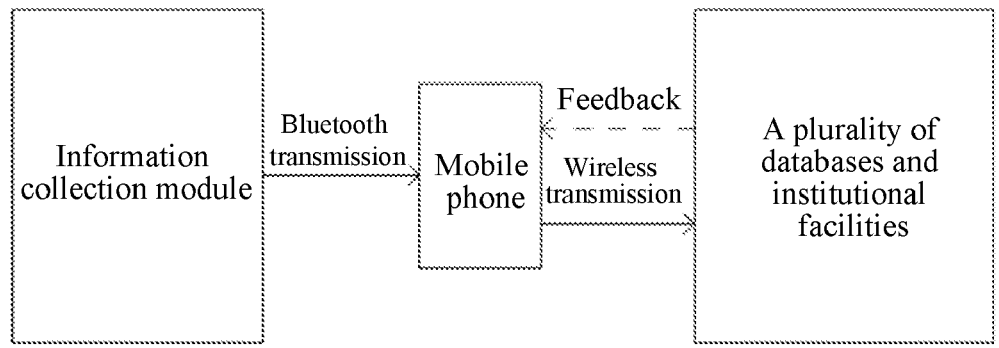
FIG. 1
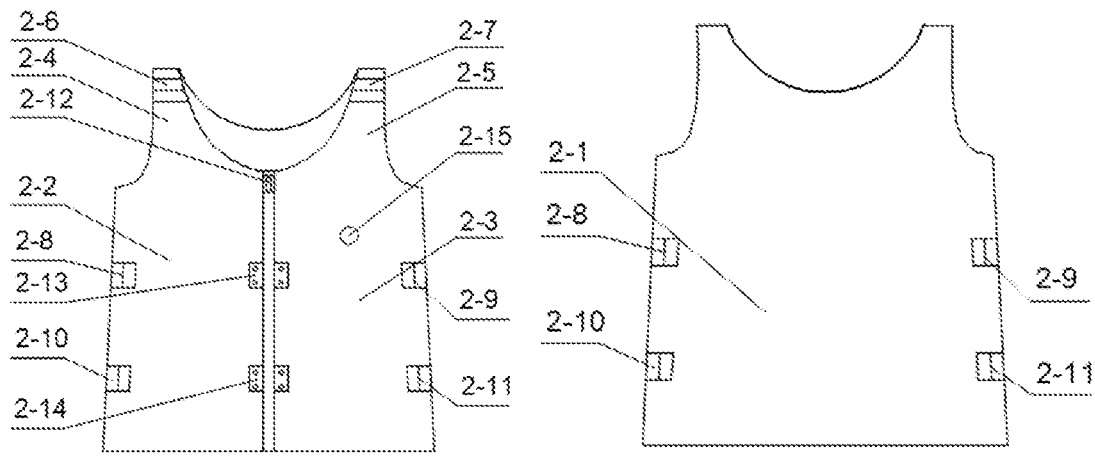
FIG. 2(a)    FIG. 2(b)
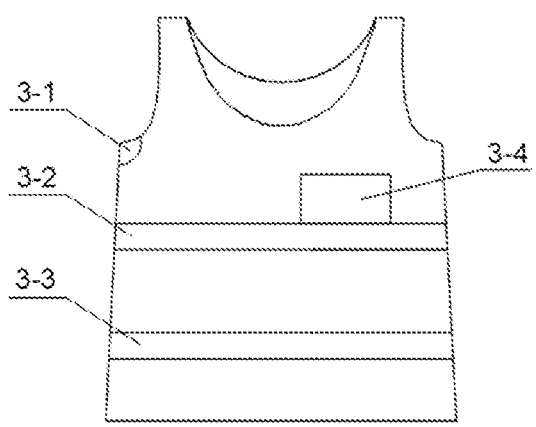 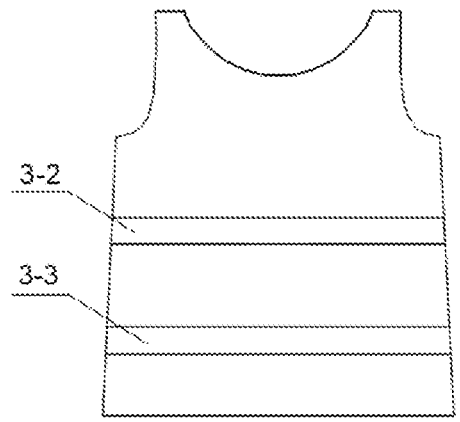
FIG. 3(a)    FIG. 3(b)

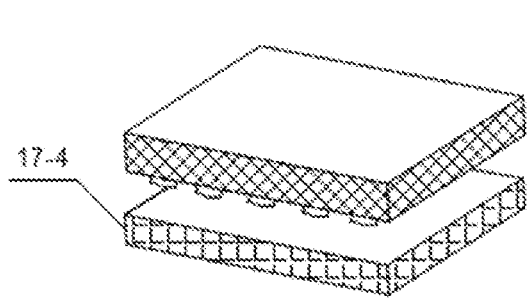
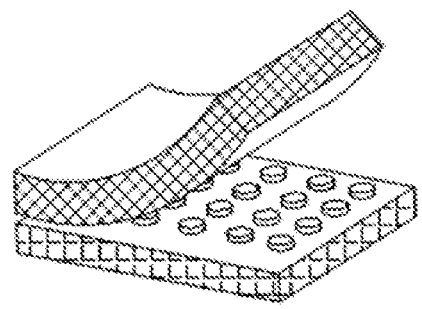
FIG. 17(c)     FIG. 17(d)
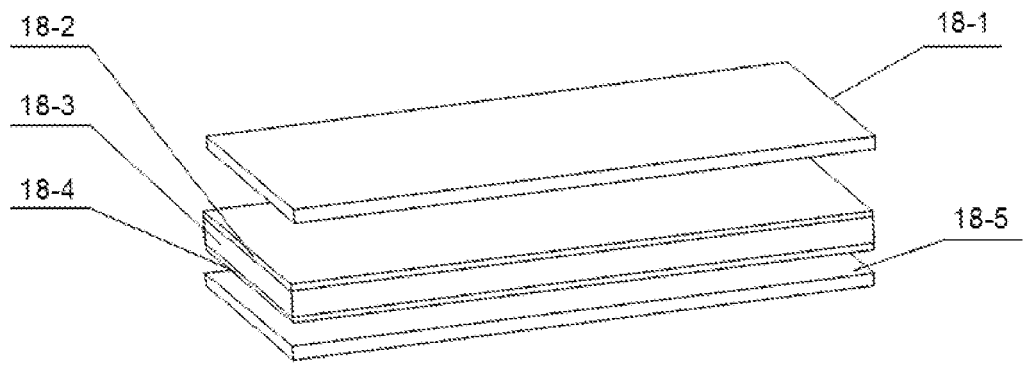
FIG. 18
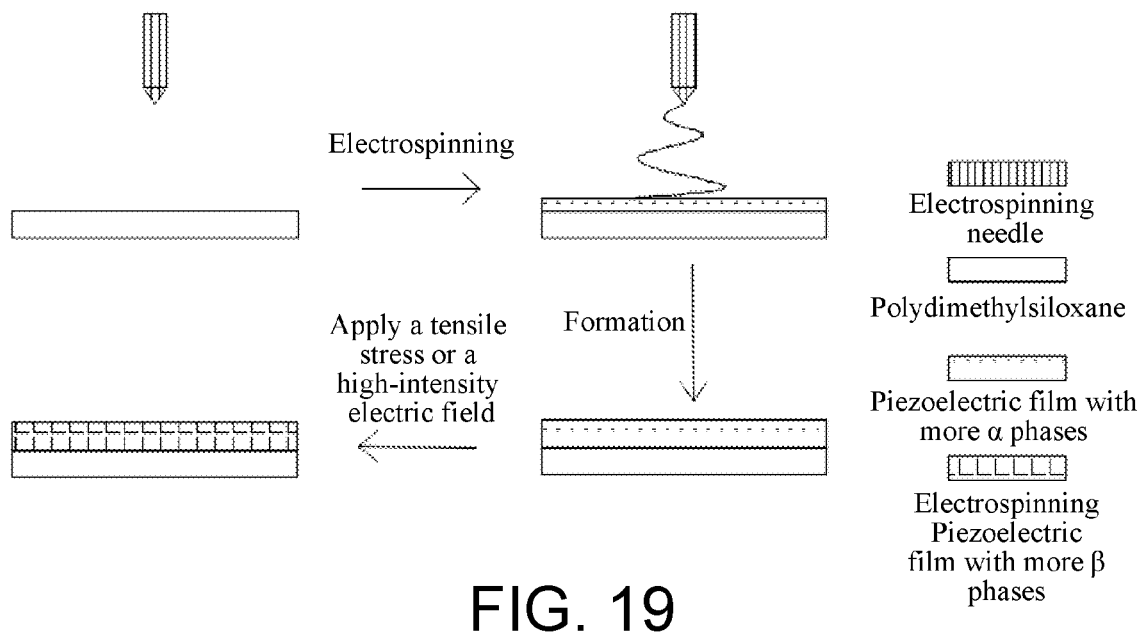
FIG. 19

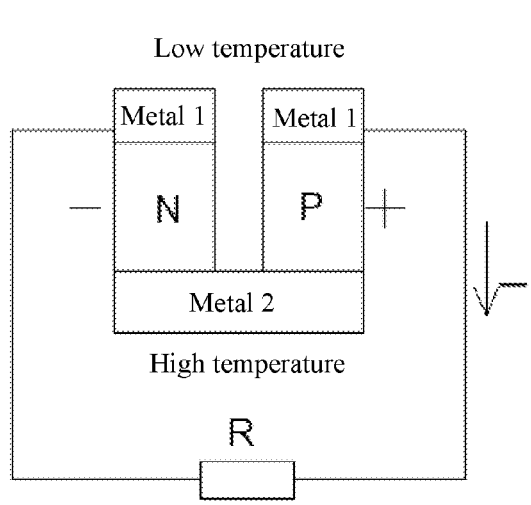
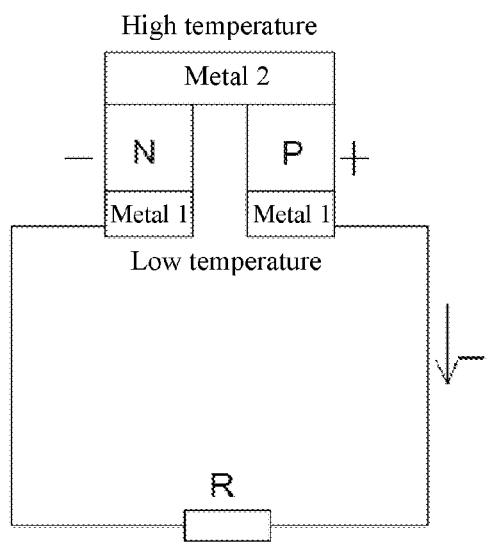
FIG. 20(a)  FIG. 20(b)
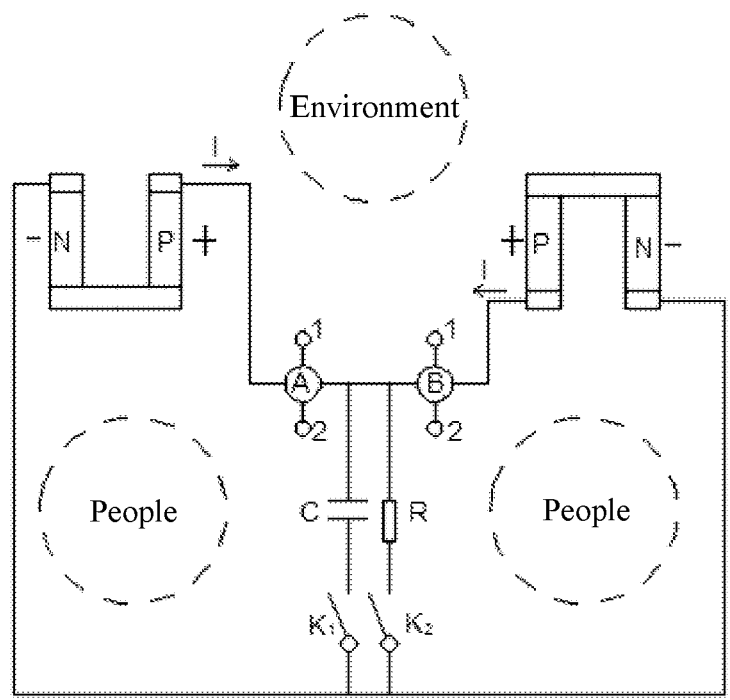
FIG. 21

FLEXIBLE SENSOR DETECTION SYSTEM FOR MEDICAL CARE AND HEALTH

CROSS-REFERENCE TO RELATED APPLICATION

This application is a 371 of international application of PCT application serial no. PCT/CN2020/074403, filed on Feb. 6, 2020, which claims the priority benefit of China application no. 202010048290.2, filed on Dec. 31, 2019. The entirety of each of the above mentioned patent applications is hereby incorporated by reference herein and made a part of this specification.

BACKGROUND

Technical Field

The present invention relates to the technical field of medical care and health, and in particular, to a flexible sensor detection system for medical care and health.

Related Art

The description in this section merely provides background information related to the present invention and does not necessarily constitute the prior art.

With the rapid development of science and technology today, convenience, intelligence, and environmental protection have become the development themes of various industries. Traditional medical treatment exists as a special industry. The uniqueness and closeness of the system of the traditional medical treatment increasingly expose shortcomings of traditional medical procedures, which cannot keep up with needs of people.

With the rapid development of sensing technologies and the gradual penetration of internet technologies into various fields, the combination of medical care and health fields with the sensing technologies and the internet can improve the disadvantages of a traditional medical treatment mode, and has great practical significance. The sensing technologies can measure a biological signal of a user, and transmit information to a device or an institution by information transmission, and give feedback to the user with an analysis of the information by the device or institution. Therefore, an internet-based wearable intelligent sensing device emerges at the right moment.

One of the most important parts of the wearable device is an information collection part, and whether a sensor used for information collection is flexible or rigid determines a comfort level and a measurement accuracy of the wearable device. A flexible sensor has two characteristics of being comfortable and accurate when being used in the medical care and health fields. A Rigid sensor is basically flat, hard and undeformable, and form a point-to-face, hard-to-soft contact interface when being integrated in a human body. In contrast, a flexible sensor is soft, deformable, and easy to form a face-to-face, soft-to-soft contact interface when being integrated in a human body, thus implementing more comfortable and accurate medical care and health monitoring.

At present, many patents have conducted researches on the wearable intelligent sensing device. For example:

The prior art discloses an intelligent sensing vest. The vest is used as a carrier. A chest breathing band is arranged below a chest of the vest, an abdominal breathing band is arranged at an abdomen position, a snapping-type sensor connection port is arranged outside the chest position, a battery connection port is arranged at a middle of a right shoulder band, and the chest breathing band and the abdominal breathing band support collection of a heart rate, an electrocardiogram and a breathing parameter. A wireless sensor is installed at the sensor connection port, and the wireless sensor is used for sending a physical sign parameter collected by the chest breathing band and the abdominal breathing band to an external monitoring device through wireless transmission of an electrical signal.

The prior art discloses a wearable physiological sensing device. Using a wristband as a carrier, the device is provided with an index collection and calculation unit, a microprocessor unit, a data storage unit, a wireless sending unit, a power management unit, a vibration sensor, a wireless receiving unit, and a display device.

The prior art discloses a single-chip-based intelligent wearable device, which includes a control module, a gesture detection module, a temperature collection module, a communication module, and a display module. The temperature collection module and the gesture detection module detect a physical sign signal of a user in real time and send the signal to the control module for processing. The control module determines a human body activity state according to the signal sent by the gesture detection module, displays a determination result in the display module, and sends the result to an upper computer through the communication module.

In the wearable intelligent sensing devices, the information measured by the sensor is stored by a storage device and transmitted to an external monitoring device wirelessly, but a clear feedback is not given to the user. In addition, use of a lithium polymer battery has also caused a certain degree of environmental pollution.

The prior art discloses an intelligent medical system based on a Zigbee technology. The system includes a first sensor module, a second sensor module, an alarm module, an intelligent watch, and a plurality of Zigbee coordinators. Each Zigbee coordinator is communicated with a server through a gateway device. The first sensor module is configured to detect a condition of a ward, the second sensor module is configured to detect a condition of a corridor outside the ward, and the intelligent watch is used to detect a physiological condition of a patient in the ward. The first sensor module, the second sensor module, and the alarm module communicate with the server through the Zigbee coordinators, and the intelligent watch directly communicates with the server through the gateway device, so as to implement temperature and humidity detection as well as fire monitoring and alarming in the ward. In addition, a doctor and a nurse can query detailed information of the patient.

This monitoring system is limited in a certain space, and cannot carry out real-time medical monitoring on the user in any space.

SUMMARY

To solve the foregoing problems, the present invention discloses a flexible sensor detection system for medical care and health, which can better detect physical sign parameters of a user by using a flexible sensor, reduce environmental pollution by using a heat-electricity conversion device to supply power, and transmit and feed back data by using a mobile phone and an internet, so that the user and an institution as a whole can be regarded as an Internet of Things, and data can be transmitted and fed back in real time.

In some implementations, the following technical solutions are used:

A flexible sensor detection system for medical care and health, including:
- an information collection module, which uses a wearable device as a carrier, where flexible sensors are respectively arranged on the wearable device, and used for collecting a heart rate parameter, an electrocardiogram (ECG) parameter, a breathing parameter, a temperature parameter, a blood flow rate parameter, a blood glucose parameter, and a blood oxygen parameter in real time;
- an information transmission module, configured to wirelessly transmit the collected information to an information processing and feedback module; and
- the information processing and feedback module, configured to perform grading treatment on received data information and feed back a health condition corresponding to the data information to the information transmission module, where the information transmission module compares feedback health condition data with a preset health threshold to determine whether to give an alarm.

A preparation process of the flexible sensor is as follows:
- processing a sensitive material by using a photoetching technology to process the same into a set functional layer shape;
- transferring the processed functional layer to a flexible substrate by using a transfer printing technology;
- photoetching on a conductive metal to process the same into a set electrode shape; and
- flexibly packaging an electrode and a sensitive layer on the flexible substrate to prepare the same into the flexible sensor.

The wearable device includes: a wearable vest; the wearable vest includes a vest back piece, a vest left front piece, and a vest right front piece; an inner side face of a front chest in the vest right front piece is provided with a heart rate ECG band for collecting the heart rate parameter and the ECG parameter of a wearer; a breathing band is arranged on an abdomen inside the vest left front piece, the right front piece, and the vest back piece, which surrounds the body by one circle for collecting the breathing parameter, and a shell temperature band is arranged at an armpit inside the vest left front piece for collecting a shell temperature parameter; an outer side face of the vest right front piece is provided with a first master control chip used for storing a plurality of physical sign parameters collected by using the vest as a carrier; and the heart rate ECG band, the breathing band, and the shell temperature band are respectively connected to the first master control chip.

The wearable device further includes: a wristband, where an inner side of the wristband is provided with a blood flow rate band for collecting the blood flow rate parameter; the inner side of the wristband is provided with a blood glucose band for collecting the blood glucose parameter; an outer side face of a wristband body is provided with a second master control chip used for storing a plurality of physical sign parameters collected by using the wristband as a carrier; and the blood flow rate band and the blood glucose band are respectively connected to the second master control chip.

The wearable device further includes: a headband connecting a head and a tail of a banded structure through an adjustable button; an inner side of the headband is provided with a blood oxygen band for collecting the blood oxygen parameter, and the headband is provided with a deep temperature band for collecting a deep temperature parameter; an outer side face of the headband is provided with a third master control chip used for storing a plurality of physical sign parameters collected by using the headband as a carrier; and the blood oxygen band and the deep temperature band are respectively connected to the third master control chip.

Compared with the prior art, the present invention has the following beneficial effects:
(1) The vest is used as the carrier of information collection, which can be close to a body of a user and facilitate the collecting operation of the sensors. In addition, the design of the adjustable buttons may be adjusted according to a physical sign of people, which meets a wearing comfort level of people, and makes sensing elements close to a body surface of people, thus increasing the measurement accuracy. The design of the zipper is convenient for people to wear.
(2) The heart rate ECG band, the breathing band, the shell temperature band, the blood flow rate band, the blood glucose band, the blood oxygen band, and the deep temperature band are provided with the built-in flexible sensors, and support the collection of parameters such as a heart rate parameter, an ECG parameter, a breathing parameter, a temperature parameter, a blood glucose parameter, and a blood oxygen parameter. In addition, the flexible sensors have the characteristics of portability and stretchability, and give the user more comfortable experience.
(3) The battery based on a thermal-electrical conversion device, an optical-electrical conversion device, or a dynamic-electrical conversion device reduce the dependence on a traditional chemical battery and reduce the environmental pollution. In addition, through a circuit design, the designed thermal-electrical conversion device can ensure that the vest is always in a working state to collect information of the user at all times, so as to facilitate subsequent analysis and processing and give feedback to the user.
(4) The main control chip transmits the physical parameters of the user to a mobile phone via Bluetooth®, and a health pre-value alarm device provided in the mobile phone can respond to a sudden emergency disease of the user. In addition, the mobile phone periodically sends physical sign parameter information of the user to a database for analysis and processing, and sends a health condition to the mobile phone for the user to view.
(5) By analyzing and processing the data hierarchically through the database, the received data can be discriminated in a more detailed way, and an analysis result can be processed differently and feedback can be given to the user. If the user is in a healthy or sub-healthy state, a corresponding form is sent to the mobile phone; if the user has a slight or serious disease, a form is sent to the mobile phone, and information is transmitted to a relevant institution and the patient is arranged for a medical treatment.

BRIEF DESCRIPTION OF THE DRAWINGS

FIG. 1 is an overall structural diagram of a flexible sensor detection system for medical care and health according to an embodiment of the present invention.

FIG. 2(*a*) to FIG. 2(*b*) are front and rear views of a vest according to an embodiment of the present invention.

FIG. 3(a) to FIG. 3(b) are front and rear views of a shell temperature band, a breathing band, and a heart rate ECG band in a vest position according to an embodiment of the present invention.

FIG. 17(a) to FIG. 17(d) are flow charts of a transfer printing technology according to an embodiment of the present invention.

FIG. 18 is a layered structural diagram of a flexible heart rate sensor and a flexible breathing sensor based on piezoelectric effect according to an embodiment of the present invention.

FIG. 19 is a flow chart of an electrostatic spinning technology according to an embodiment of the present invention.

FIG. 20(a) to FIG. 20(b) are respectively schematic diagrams of thermal-electrical conversion according to an embodiment of the present invention.

FIG. 21 is a diagram showing that a thermal-electrical conversion battery module supplies power to a sensing module according to an embodiment of the present invention.

DETAILED DESCRIPTION

Figure 4A:
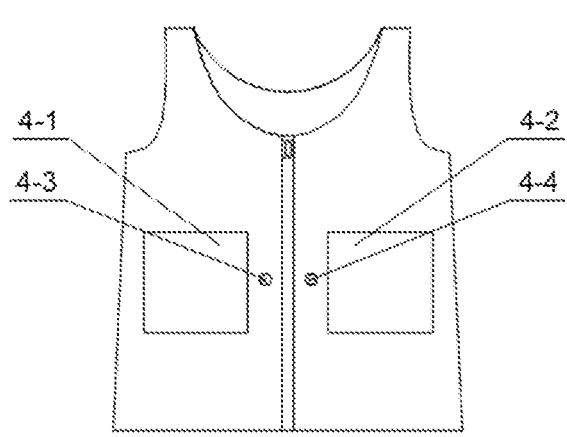
FIG. 4(a) to FIG. 4(b) are front and rear views of a battery module in a vest position according to an embodiment of the present invention.

It should be noted that the following detailed descriptions are all exemplary and are intended to provide further descriptions of this application. Unless otherwise specified, all technical and scientific terms used in the present invention have the same meaning as commonly understood by a person of ordinary skill in the art to which this application belongs.

It should be noted that terms used herein are only for describing specific implementations and are not intended to limit exemplary implementations according to this application. As used herein, the singular form is intended to include the plural form, unless the context clearly indicates otherwise. In addition, it should be further understood that terms "include" and/or "comprise" used in this specification indicate that there are features, steps, operations, devices, assemblies, and/or combinations thereof.

Embodiment 1

In one or more embodiments, a flexible sensor detection system for medical care and health is disclosed, as shown in FIG. 1, including:

an information collection module, which uses a vest, a wristband, and a headband as carries, which are respectively provided with flexible sensors, and used for collecting a heart rate parameter, an electrocardiogram (ECG) parameter, a breathing parameter, a temperature parameter, a blood flow rate parameter, a blood glucose parameter, and a blood oxygen parameter in real time;

an information transmission module, configured to transmit the collected information to an information processing and feedback module via Bluetooth®; and the information processing and feedback module, configured to perform grading treatment on received data information and feed back a health condition corresponding to the data information to the information transmission module, where the information transmission module compares feedback health condition data with a preset health threshold to determine whether to give an alarm.

In this embodiment, a mobile phone terminal is used as the information transmission module. The mobile phone terminal acts as an intermediary for information transmission, and is used to store personal information of a user and information sent by the information collection module, wirelessly send the information to the information processing and feedback module with a period of days, and receive health condition feedback sent by the information processing and feedback module and related institutions. In addition, the mobile phone terminal also acts as an alarm system. When the information sent by the information collection module exceeds a preset value of human health set in the mobile phone, the mobile phone terminal directly reports to a nearby hospital, and the hospital takes measures to come to the rescue.

In this embodiment, the information processing and feedback module is a plurality of databases and institutional facilities. The information processing and feedback module receives data about physical sign parameters, personal information, and geographical location of the user sent by the mobile phone, and analyzes and processes the received physical sign parameters of the user step by step. Through analysis and processing, a health status of the user is sent to the mobile phone terminal in a form to give the user feedback. In addition, the alarm information sent by the mobile phone terminal is processed and fed back urgently.

Specifically, a structure of the vest is as shown in FIG. 2(a) to FIG. 2(b), and a processing fabric of the vest is made of CoolMax fiber, which ensures a wearing comfort of the user. A vest body includes a vest back piece 2-1, a vest left front piece 2-2, a right front piece 2-3, a left shoulder band 2-4 for connecting the vest back piece 2-1 and the vest left front piece 2-2, and a right shoulder band 2-5 for connecting the vest back piece 2-1 and the right front piece 2-3.

The vest is made by sewing the vest left front piece 2-2, the vest back piece 2-1 and the right front piece 2-3 into a tubular shape in turn, where the left shoulder band 2-4 of the vest is provided with an adjustable button 2-6 of the left shoulder band and the right shoulder band 2-5 of the vest is provided with an adjustable button 2-7 of the right shoulder band. An adjustable button 2-8 below a left chest and an adjustable button 2-10 at a left abdomen position are respectively arranged at a boundary between the vest left front piece 2-2 and a left side of the vest back piece 2-1. An adjustable button 2-9 below a right chest and an adjustable button 2-11 at a right abdomen position are respectively arranged at a boundary between the right front piece 2-3 and a right side of the vest back piece 2-1. An opening zipper 2-12 is arranged between the vest left front piece 2-2 and the right front piece 2-3, and the opening zipper 2-12 extends all the way to a neckline. The vest is respectively provided with a connector interface 2-13 and a connector interface 2-14 of the breathing band below the chest and at the abdomen position at two sides of the zipper. Sensitive layers inside the breathing bands of the vest left front piece and the vest right front piece are connected through the connector interfaces to form a closed flexible breathing sensor around a human body one circle to make the flexible breathing sensor work normally.

The vest is provided with a vest main control chip 2-15 on the right front piece 2-3. For the sake of beauty, an appearance of the vest main control chip 2-15 is made into a badge style.

A sensing module on the vest includes a shell temperature band 3-1, a chest breathing band 3-2, an abdominal breathing band 3-3, a heart rate ECG band 3-4, and the vest main control chip 2-15. Arrangements of the shell temperature band 3-1, the chest breathing band 3-2, the abdominal breathing band 3-3, and the heart rate ECG band 3-4 in the vest are as shown in FIG. 3(a) to FIG. 3(b). The shell temperature band 3-1 is arranged at an armpit position of the vest left front piece 2-2 for collecting a parameter such as shell temperature. The chest breathing bands 3-2 and the abdominal breathing bands 3-3 are respectively arranged below the chest and at the abdominal position of the vest left front piece 2-2, below the chest and at the abdominal position of the right front piece 2-3, and below the chest and at the abdominal position of the vest back piece 2-1. The chest breathing band 3-2 and the abdominal breathing band 3-3 are arranged surrounding the body by one circle for collecting breathing parameters. The heart rate ECG band 3-4 is arranged at the chest position of the right front piece 2-3 for collecting heart rate and ECG parameters. The shell temperature band 3-1, the chest breathing band 3-2, the abdominal breathing band 3-3, and the heart rate ECG band 3-4 are each sewed on corresponding positions of the vest and sensing parts are located on an inner side face of the vest. The vest main control chip 2-15 is used for storing physical sign parameters measured by the shell temperature band 3-1, the chest breathing band 3-2, the abdominal breathing band 3-3, and the heart rate ECG band 3-4, and transmitting the physical sign parameters to a mobile phone terminal via Bluetooth®.

Figure 4B:
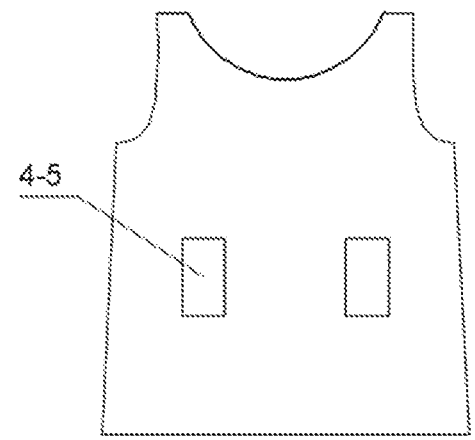

A battery module on the vest includes a left battery unit 4-1, a right battery unit 4-2, a temperature switch A4-3, a temperature switch B4-4, and a power storage unit 4-5. An arrangement of the battery module on the vest is as shown in FIG. 4(a) to FIG. 4(b). The vest left front piece 2-2 is provided with the left battery unit 4-1, the right front piece 2-3 is provided with the right battery unit 4-2, the vest left front piece 2-2 and the right front piece 3 are provided with the temperature switch A4-3 and the temperature switch B4-4, and the vest back piece 2-1 is provided with the power storage unit 4-5.

Figure 5:
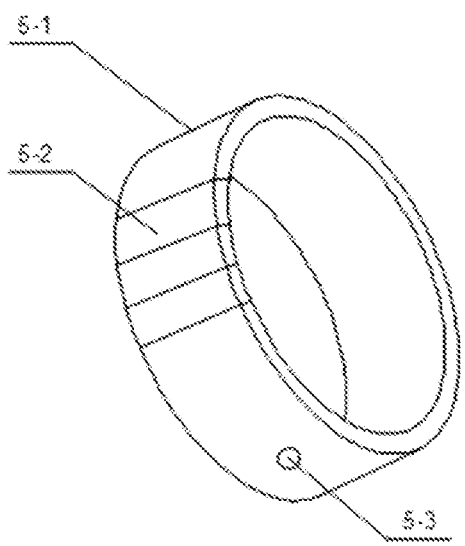
FIG. 5 is a schematic diagram of a wristband according to an embodiment of the present invention.

A structure of the wristband is as shown in FIG. 5, where a strip structure is connected end to end to form a wristband body 5-1, and the wristband body 5-1 is woven by CoolMax fiber. A position where the strip structure connected end to end is provided with a wristband adjustable button 5-2, and the wristband body 5-1 is provided with a wristband main control chip 5-3. For the sake of beauty, an appearance of the wristband main control chip 5-3 is made into an icon style.

Figure 6:
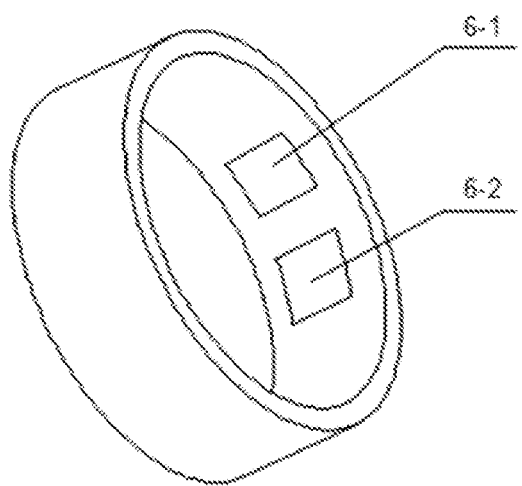
FIG. 6 is a position diagram of a blood flow rate band and a blood glucose band in a wristband according to an embodiment of the present invention.

A sensing module on the wristband includes a blood flow rate band 6-1, a blood glucose band 6-2, and the wristband main control chip 5-3. Arrangements of the blood flow rate band 6-1 and the blood glucose band 6-2 on the wristband are as shown in FIG. 6. The blood flow rate band 6-1 is used for collecting parameters like blood flow rate, the blood glucose band 6-2 is used for collecting parameters like blood glucose. The blood flow rate band 6-1 and the blood glucose band 6-2 are each arranged on corresponding positions of the wristband, and sensing parts are located on an inner side of the wristband. The wristband main control chip 5-3 is used for storing physical sign parameters measured by the blood flow rate band 6-1 and the blood glucose band 6-2, and transmitting the physical sign parameters to a mobile phone terminal via Bluetooth®.

Figure 7:
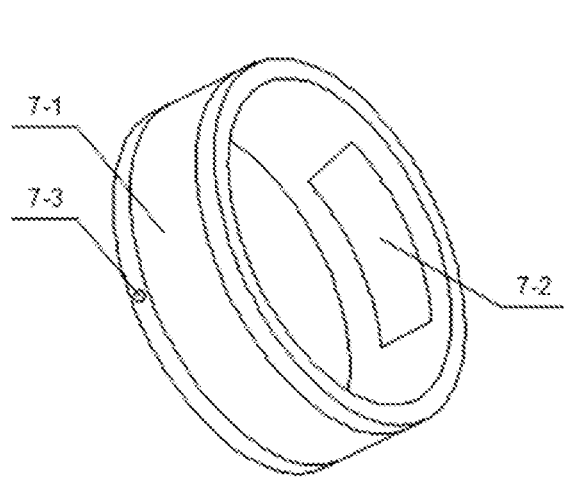
FIG. 7 is a position diagram of a battery unit in a wristband according to an embodiment of the present invention.

A battery module on the wristband includes a wristband battery unit 7-1, a wristband power storage unit 7-2, and a wristband light sensing switch 7-3. Arrangements of the battery module on the wristband are as shown in FIG. 7. The wristband battery unit 7-1 and the wristband power storage unit 7-2 are arranged on the wristband body 5-1, while the wristband light sensing switch 7-3 is arranged at an outer side of the wristband.

Figure 8:
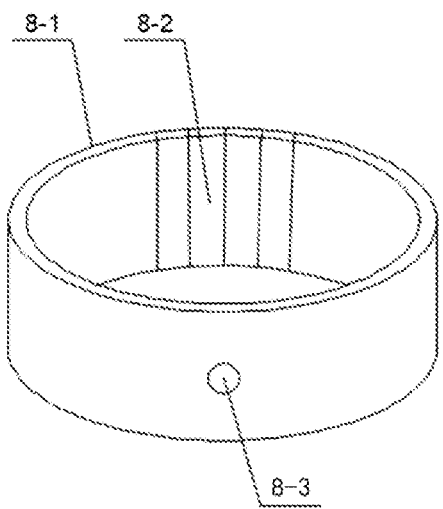
FIG. 8 is a schematic diagram of a headband according to an embodiment of the present invention.

A structure of the headband is as shown in FIG. 8, where a strip structure is connected end to end to form a headband body 8-1, and the headband body 8-1 is woven by CoolMax fiber. A position where the strip structure connected end to end is provided with a headband adjustable button 8-2, and the headband body 8-1 is provided with a headband main control chip 8-3. For the sake of beauty, an appearance of the headband main control chip 8-3 is made into an icon style.

Figure 9:
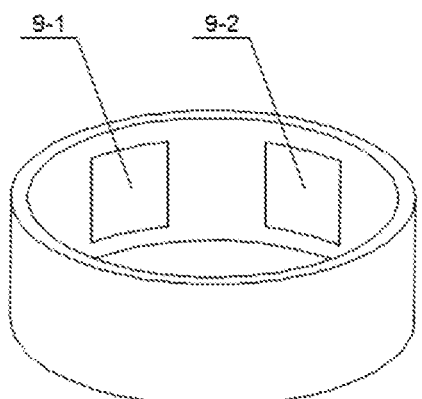
FIG. 9 is a position diagram of a blood oxygen band and a deep temperature band in a headband according to an embodiment of the present invention.

A sensing module on the headband includes a blood oxygen band 9-1, a deep temperature band 9-2, and the headband main control chip 8-3. Arrangements of the blood oxygen band 9-1 and the deep temperature band 9-2 on the headband are as shown in FIG. 9. The blood oxygen band 9-1 is used for collecting parameters like blood oxygen, the deep temperature band 9-2 is used for collecting parameters such as an internal temperature of a human body. The blood oxygen band 9-1 and the deep temperature band 9-2 are each arranged on corresponding positions of the headband, and sensing parts are located on an inner side of the headband. The headband main control chip 8-3 is used for storing physical sign parameters measured by the blood oxygen band 9-1 and the deep temperature band 9-2, and transmitting the physical sign parameters to a mobile phone via Bluetooth®.

Figure 10:
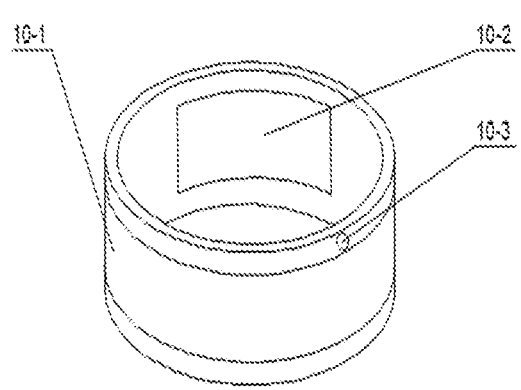
FIG. 10 is a position diagram of a battery unit in a headband according to an embodiment of the present invention.

A battery module on the headband includes a headband battery unit 10-1, a headband power storage unit 10-2, and a headband light sensing switch 10-3. Arrangements of the battery module on the headband are as shown in FIG. 10. The headband battery unit 10-1 and the headband power storage unit 10-2 are arranged on the headband body 8-1, while the headband light sensing switch 10-3 is arranged at an inner side of the headband.

In this embodiment, the adjustable buttons are made of plastic in view of weight. The adjustable buttons can adjust sizes of the vest, the wristband and the headband to meet different body types and make people feel comfortable. In addition, the adjustable buttons at the shoulder bands of the vest can also adjust the shell temperature band, so that the shell temperature band at the armpit position can be accurately located under the armpits of people with different physical signs, thus increasing the measurement accuracy. The adjustable buttons at the boundary between the vest left front piece and the left side of the vest back piece and at the boundary between the vest right front piece and the right side of the vest back piece can make the heart rate ECG band and the breathing band close to the human body, so that relevant physical sign signals are conveniently collected. The adjustable buttons at the wristband can make the blood flow rate band and the blood glucose band close to the skin, so that relevant physical sign signals are conveniently collected. The adjustable buttons at the headband can make the blood oxygen band and the deep temperature band close to the skin, so that relevant physical sign signals are conveniently collected.

In this embodiment, the heart rate ECG band internally contains a transformer, a flexible heart rate sensor, a signal amplifying circuit, an A/D converting circuit, a flexible ECG sensor and an AD8232 chip. The breathing band internally contains a transformer, a capacitor three-point resonant circuit, a flexible breathing sensor, and a breathing control chip. The shell temperature band internally contains a transformer, a signal amplifying circuit, an A/D converting circuit, and a deep temperature control chip. The blood flow rate band internally contains a transformer, a flexible blood flow rate sensor, and a blood flow rate control chip. The blood glucose band internally contains a transformer, a flexible blood glucose sensor and a blood glucose control chip. The blood oxygen band internally contains a transformer, a flexible blood oxygen sensor and a blood oxygen control chip. The deep temperature band internally contains a transformer, a flexible deep temperature sensor, a signal amplifying circuit, an A/D converting circuit, and a deep temperature control chip.

The flexible shell temperature sensor, the flexible heart rate sensor, the flexible breathing sensor, the flexible blood flow rate sensor, the flexible blood glucose sensor, the flexible blood oxygen sensor, and the flexible deep temperature sensor are each made of a flexible base layer, a functional layer and a flexible encapsulation layer, which are installed on an inner surface of a carrier, so that the sensors are in direct contact with a human body surface. Therefore, it is necessary to consider not only stretchable and compressible characteristics of the sensor, but also a biocompatibility between the sensor and the human body. Therefore, materials used for the flexible substrate and the encapsulation layer shall satisfy the following points:
 (1) the materials shall have excellent elastic mechanical properties;
 (2) the materials shall have excellent waterproof and breathable effects; and
 (3) the materials can adapt to a complicated morphology of the human body surface.

In this way, the following can be achieved:
 (1) the sensors can improve the measurement of the physical sign parameters of the human body;
 (2) sweat secreted by skin sweat glands under the sensing devices can be discharged into the air through the devices in the form of steam, so as to avoid the accumulation of sweat to form impregnation; and
 (3) outside air can pass through the devices to reach a skin surface to complete a breathing activity on the body surface.

Meanwhile, the materials have good water resistance, so that neither external liquid nor sweat on the body surface can enter the functional layers of the devices to result in short circuit failure.

Figure 11:
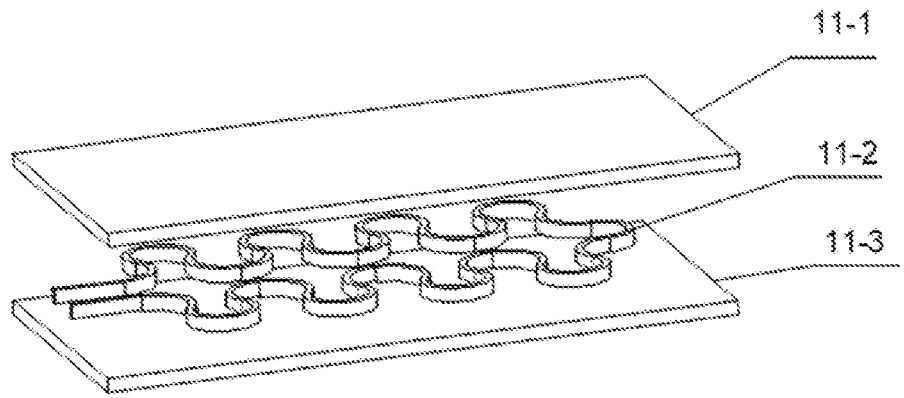
FIG. 11 is a layered structural diagram of a flexible shell temperature sensor and a flexible heart rate sensor according to an embodiment of the present invention.

The functional layers of different flexible sensors are different. For the functional layers of the flexible shell temperature sensor and the flexible heart rate sensor, a "snake-shaped" interconnection structure may be constructed, which has good mechanical properties. For the materials of the functional layer, metal with good physical properties may be selected or a conductive filler may be doped in a polymer to obtain sensitive materials with higher physical properties. Layered structures of the flexible shell temperature sensor and the flexible heart rate sensor are as shown in FIG. 11, including: an encapsulation layer 11-1 of the flexible shell temperature sensor and the flexible heart rate sensor, a functional layer 11-2 of the flexible shell temperature sensor and the flexible heart rate sensor, and a base layer 11-3 of the flexible shell temperature sensor and the flexible heart rate sensor.

The flexible shell temperature sensor and the flexible heart rate sensor are served as inductive elements of shell temperature and heart rate circuits. When the functional layer receives temperature or vibration signals, resistance of the inductive elements changes accordingly, causing current changes, thus converting the temperature or vibration signals into electrical signals. After signal amplification and A/D conversion, physical parameters of shell temperature and heart rate are obtained and stored in the vest main control chip 2-15.

Figure 12:
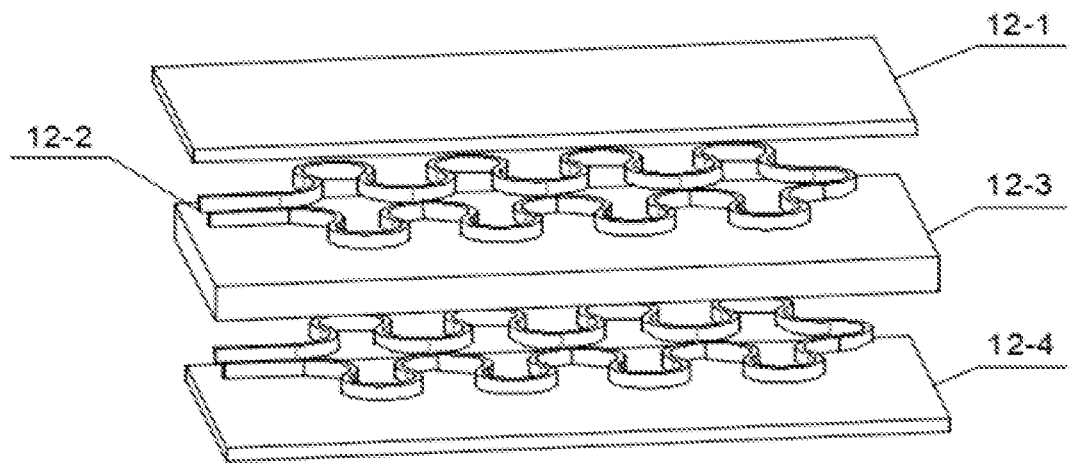
FIG. 12 is a layered structure diagram of a flexible deep temperature sensor according to an embodiment of the present invention.

The functional layer of the flexible deep temperature sensor also adopts the "snake-shaped" interconnection structure. For the materials of the functional layer, metal with good physical properties may be selected or a conductive filler may be doped in a polymer to obtain sensitive materials with higher physical properties. A layered structure of the flexible deep temperature sensor is as shown in FIG. 12, including: an encapsulation layer 12-1 of the flexible deep temperature sensor, a functional layer 12-2 of the flexible deep temperature sensor, an isolation layer 12-3 of the flexible deep temperature sensor, and a base layer 12-4 of the flexible deep temperature sensor. The two flexible temperature sensors are integrated and separated by a polymer. A measurement principle is to use a differential measurement mode of a plurality of temperature sensors to measure the deep temperature of the human body in a non-intrusive manner. The flexible deep temperature sensor is served as an inductance element of a deep temperature circuit. When the functional layer receives temperature signals, resistance of the inductive element changes accordingly, causing current changes, thus converting the temperature signals into electrical signals. After signal amplification and A/D conversion, a temperature value is obtained. The deep temperature control chip calculates a deep temperature according to the measured temperature value through a corresponding algorithm and transmits the deep temperature to the headband main control chip 8-3.

Figure 13:
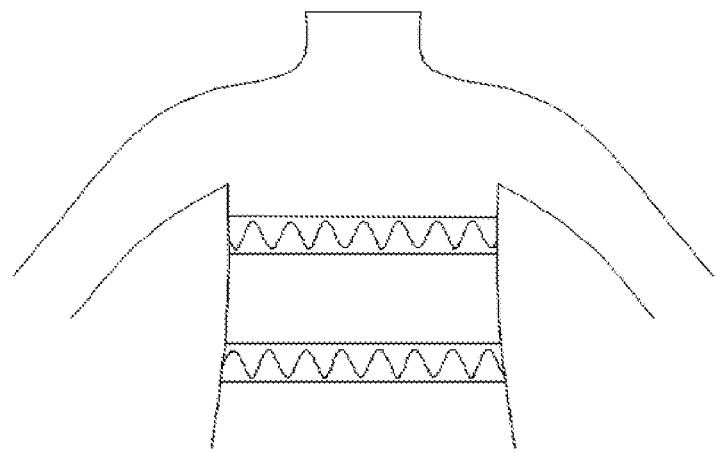
FIG. 13 is a coil structure of a flexible breathing sensor according to an embodiment of the present invention.

The functional layer of the flexible breathing sensor adopts an insulated coil bent into a certain shape. The coil needs to form a closed loop in the chest and abdomen of the user respectively, as shown in FIG. 13. The coil is served as an inductive element of a capacitor three-point resonant circuit. A breathing movement causes the change of inductance of the coil, which leads to the change of resonance conditions of a resonant circuit, thus causing a resonance amplitude and a resonance frequency to change with the breathing movement. The breathing control chip is used for analyzing and processing the resonance amplitude and the resonance frequency, obtaining physical sign parameters of the breathing movement by frequency modulation-detection, and transmitting the parameters to the vest main control chip 2-15.

A connector interface 2-13 of the breathing band at the chest position and a connector interface 2-14 of the breathing band at the abdominal position connect the flexible breathing sensors in the chest breathing band 3-2 and the abdominal breathing band 3-3 to form a closed sensor around the human body by one circle to make the sensor work normally.

A working principle of the flexible blood flow rate sensor is to measure the blood flow rate by a thermal method, which will cause temporal and spatial distribution and changes of a temperature field on the body surface, and can deduct the blood flow rate by monitoring the changes through the temperature sensor, combining with a heat transfer model or a correlation analysis.

Figure 14:
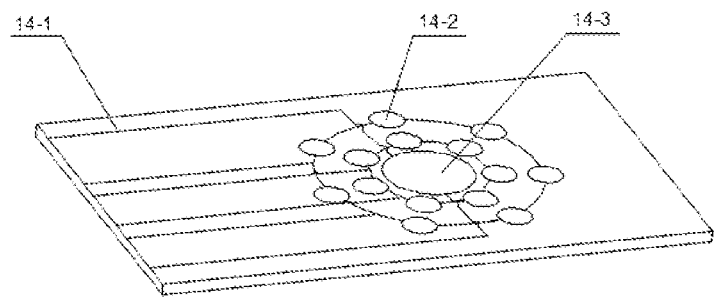
FIG. 14 is a functional layer of a flexible blood flow rate sensor according to an embodiment of the present invention.

The functional layer of the flexible blood flow rate sensor is as shown in FIG. 14. A central position of the functional layer is provided with a central heater 14-3 for artificially manufacturing a temperature rise of the body surface, and two circles of temperature sensors 14-2 are distributed around the functional layer for measuring the temperature field. The blood flow rate control chip is used for controlling the heating of the central heater, analyzing and processing the temperature field information measured by the temperature sensor to obtain physical sign parameters of the blood flow rate, and transmitting the parameters to the wristband main control chip 5-3 through a signal wireway 14-1.

The functional layer of the flexible blood glucose sensor includes a glucose sensor and a paper battery coated with a high-concentration hyaluronic acid at an anode. Glucose in a tissue fluid is extracted by using an electrochemical double-channel method, and is sensed and measured by the glucose sensor. The blood glucose control chip analyzes and processes the data measured by the glucose sensor and transmits the processed data to the wristband main control chip 5-3.

The functional layer of the flexible blood oxygen sensor is composed of a red and infrared LED and a photodetector. The red and infrared LED is served as a light source. The photodetector can obtain a light absorption degree and a light scattering degree of the blood according to an action of the blood on the light. The blood oxygen control chip analyzes and processes the data measured by the photodetector to obtain blood oxygen parameters and transmits the parameters to the headband main control chip 8-3.

Figure 15:
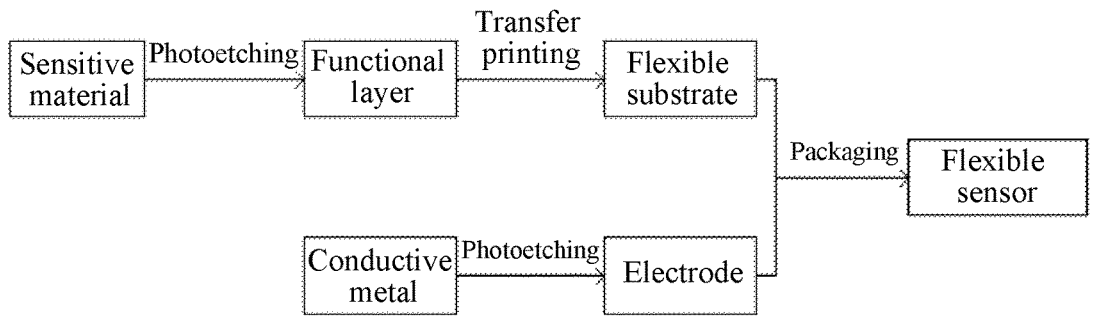
FIG. 15 is a preparation process of a flexible sensor according to an embodiment of the present invention.

A preparation process of the flexible sensor is as shown in FIG. 15. Firstly, a sensitive material is processed into a desired functional layer shape by a photoetching technology, and then the processed functional layer is moved to a flexible substrate by a transfer printing technology. Moreover, a conductive metal is photoetched into a desired electrode shape, and finally, the electrode and the sensitive layer on the flexible substrate are flexibly encapsulated to prepare the flexible sensor.

Figure 16:
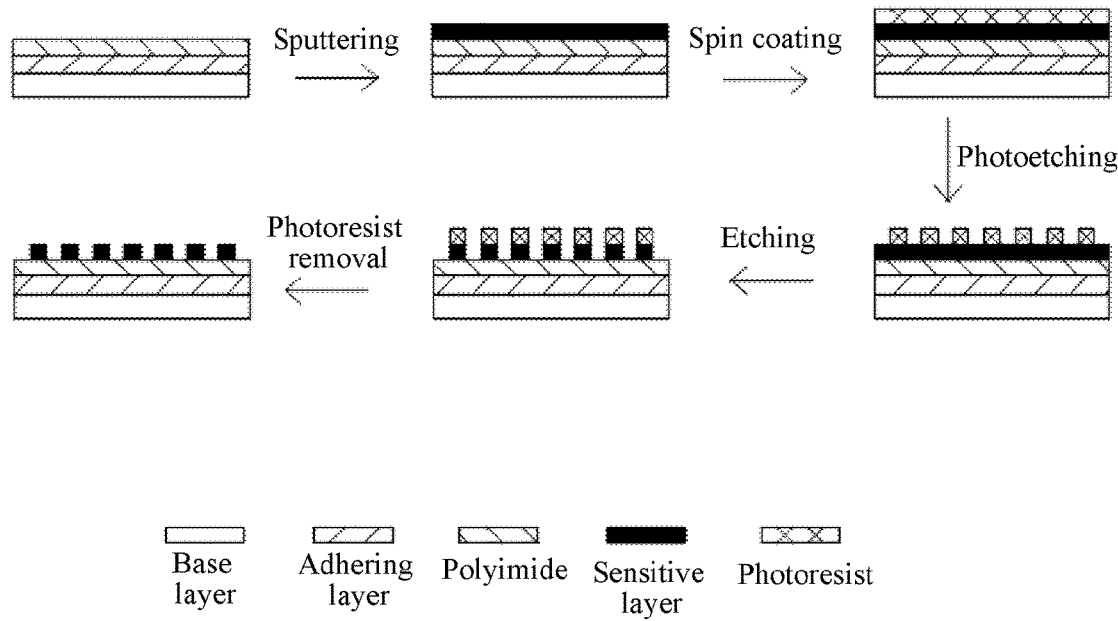
FIG. 16 is a flow chart of a photoetching technology according to an embodiment of the present invention.

FIG. 16 is a diagram of a photoetching technology, where main steps of the photoetching technology are as follows:
  (1) cleaning a substrate: a traditional photoetching technology requires a material substrate to be flat, while a flexible material such as polyimide needs to be pretreated during photoetching; the flexible material such as polyimide needs to be adhered to the clean substrate as a donor substrate; and moreover, the substrate is cleaned in a plurality of steps to ensure tight adhesion and avoid deviation caused by pollution during photoetching;
  (2) sputtering and depositing a sensitive layer: sputtering and depositing a sensitive material on the donor substrate to form a sensitive layer, where depositing techniques include chemical vapor deposition, physical vapor deposition and the like; and a suitable depositing method is selected according to different deposited materials;
  (3) gluing, exposuring and developing: designing a mask plate according to a needed pattern; uniformly coating photoresist on a surface of the sensitive layer by adjusting a rotating speed of a spin coater, and patterning the photoresist through the mask plate by the steps of dewatering baking, soft baking and hard baking, where the photoresist disappears in an exposed part, the sensitive layer is exposed, and the photoresist still exists in an unexposed part;
  (4) graphically etching the sensitive layer: etching the sensitive layer not covered by the photoresist by an etching solution to implement transfer of a mask plate pattern to a sensitive layer pattern; and
  (5) removing the photoresist and cleaning: washing with an acetone solution to remove residual photoresist and organic matters on a metal layer, and finally obtaining the desired functional layer pattern.

Figures 17A, 17B:
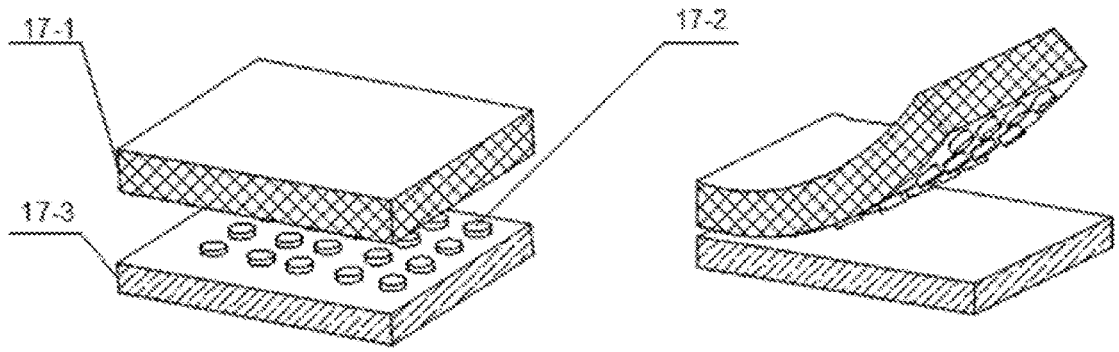

FIG. 17 (*a*) to FIG. 17(*d*) are process diagrams of the transfer printing technology, and the main steps of the transfer printing technology are as follows:
  (1) preparing a desired functional layer pattern 17-2 on a flexible material like polyimide as a donor substrate 17-3 through a photoetching technology;
  (2) processing a flexible stamp 17-1 made of polydimethylsiloxane and a surface of the functional layer pattern 17-2 to be transferred according to a set requirement, attaching the flexible stamp 17-1 closely to the functional layer 17-2, and tearing up the flexible stamp 17-1 from the donor substrate 17-3 at a high enough speed to ensure that an adhesive force between the flexible stamp 17-1 and the functional layer 17-2 is large enough, so that the functional layer 17-2 can be torn up along with the flexible stamp 17-1;

(3) attaching the flexible stamp 17-1 adhered with the functional layer 17-2 closely to a surface of a processed acceptor substrate 17-4, and extruding for a certain period to form an adhesive force between the functional layer 17-2 and the surface of the acceptor substrate 17-4; and (4) slowly tearing up the flexible stamp 17-1 to ensure that the functional layer 17-2 to be transferred remains on the acceptor substrate 17-4.

A flexible fabric electrode is used for a flexible ECG sensor to convert bioelectric signals into hardware measurable electrical signals, and an AD8232 integrated with operational amplifier, ADC digital-to-analog conversion, DSP digital filtering and heart rate detection algorithms as a front-end conditioning chip of ECG signals. The AD8232 analyzes and processes the signals measured by the flexible fabric electrode and transmits the processed ECG signals to the vest main control chip 2-15.

Measurement principles of the flexible heart rate sensor and the flexible breathing sensor may also be implemented based on piezoelectric effect. A flexible piezoelectric film material may be polyvinylidene fluoride with good piezoelectric properties and high flexibility, and the electrode may be made of metal with good physical properties. Layered structures of the flexible heart rate sensor and the flexible breathing sensor are as shown in FIG. 18, including: an encapsulation layer 18-1 of the flexible heart rate sensor and the flexible breathing sensor based on piezoelectric effect, an upper electrode 18-2 of the flexible piezoelectric film, the flexible piezoelectric film 18-3, a lower electrode 18-4 of the flexible piezoelectric film, and a base layer 18-5 of the flexible heart rate sensor and the flexible breathing sensor based on piezoelectric effect. The upper electrode 18-2 of the flexible piezoelectric film, the flexible piezoelectric film 18-3, and the lower electrode 18-4 of the flexible piezoelectric film constitute the functional layer of the flexible heart rate sensor and the flexible breathing sensor. The flexible heart rate sensor and the flexible breathing sensor are served as sensing elements of heart rate, breathing and blood pressure circuits. When the functional layer is excited by heart beating and breathing movement of a user, the flexible piezoelectric film bends. Piezoelectric charges are generated at the moment of bending, and a potential difference is generated between the upper and lower electrodes. In this way, heart rate and breathing signals of the user are converted into electrical signals. Then, the electrical signals stored with heart rate and breathing information are transmitted to the AD8232 chip and the breathing control chip respectively. After being analyzed and processed by the AD8232 chip, the breathing control chip and a blood pressure chip, the physical sign parameters of heart rate and breathing of the user are obtained and transmitted to the vest main control chip 2-15.

The flexible piezoelectric film is prepared by an electrostatic spinning method, and an electrostatic spinning technology is as shown in FIG. 19.

(1) A flexible substrate is prepared, and placed below an electrospinning needle as a collecting device of the flexible piezoelectric film, where the flexible substrate is made of polydimethylsiloxane with good flexibility.

(2) Under the action of a high-voltage electric field applied by a power supply, a surface of a piezoelectric polymer solution or a melt in a syringe pump generates electric charges, and under the combined action of an electric field force and a surface tension, a conical droplet is formed on the electrospinning needle, and is called a Taylor cone. If the voltage is continuously increased, the charged conical droplet overcomes the surface tension and is gradually lengthened and thinner, breaking through a cone top and shooting at a collection substrate, and finally forming a fibrous piezoelectric film.

(3) Generally, most of the prepared piezoelectric films are spiral nonpolar α-phases, which are stable in structure but not piezoelectric. It is necessary to apply a tensile stress or a high-intensity electric field to the films, so that randomly oriented molecular dipole moments in the piezoelectric film are aligned in a specific direction, thus forming a β-phase with good piezoelectric properties.

The adjustable button 2-6 of the left shoulder band and the adjustable button 2-7 of the right shoulder band can adjust a longitudinal size of the vest. The adjustable button 2-8 below the left chest, the adjustable button 2-10 on the left abdomen position, the adjustable button 2-9 below the right chest and the adjustable button 2-11 on the right abdomen position can adjust a lateral size of the vest. The wristband adjustable button 5-2 can adjust a diameter of the wristband. The headband adjustable button 8-2 can adjust a diameter of the headband. In this way, the vest can meet physiques of different users to increase the comfort level. Moreover, each flexible sensor can be closely attached to the human body surface by the adjustable buttons, thus increasing the measurement accuracy.

The left battery unit 4-1 and the right battery unit 4-2 adopt a principle of thermal-electrical conversion. When a P-type semiconductor and an N-type semiconductor form a loop, in the presence of an external load, if temperatures at two end faces of the P-type semiconductor and the N-type semiconductor are different and a temperature difference occurs, then a voltage and a current may be generated in the loop, where the P-type semiconductor is an anode of the battery and the N-type semiconductor is a cathode of the battery. The vest designed only works at a normal ambient temperature. According to an ambient temperature of the vest, a low-temperature thermoelectric material Bi2Te3 is selected. Adding a proper amount of Se to Bi2Te3 may obtain the N-type semiconductor needed by the thermoelectric conversion device, and adding a proper amount of Sb to Bi2Te3 may obtain the P-type semiconductor needed by the thermoelectric conversion device, where chemical formulae of the semiconductors are as follows:

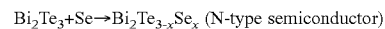
$$Bi_2Te_3 + Se \rightarrow Bi_2Te_{3-x}Se_x \text{ (N-type semiconductor)}$$

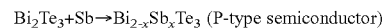
$$Bi_2Te_3 + Sb \rightarrow Bi_{2-x}Sb_xTe_3 \text{ (P-type semiconductor)}$$

FIG. 20(a) and FIG. 20(b) show two types of thermal-electrical conversion circuits, both of which take an outer side of a metal 2 as a high-temperature heat source and an outer side of a metal 1 as a low-temperature heat source to carry out analysis. Only the up-down order of the metal 1 and the metal 2 is changed, and it is found that circuits in FIG. 20(a) and FIG. 20(b) each use the P-type semiconductor as the anode and the N-type semiconductor as the cathode. The form of FIG. 20(a) is taken as a unit to connect the metal 1 and the metal 2 in series to integrate the left battery unit 4-1. Similarly, the form of FIG. 20(b) is taken as a unit to connect the metal 1 and the metal 2 in series to integrate the right battery unit 4-2.

In this embodiment, considering that a temperature difference between an external ambient temperature and a human body temperature cannot always be in the same situation, a circuit as shown in FIG. 21 is designed, where a left thermal-electrical conversion device is a simplification of the left battery unit 4-1, a right thermal-electrical conversion device is a simplification of the right battery unit 4-1, C refers to a power storage device, and R refers to a plurality of power consumption devices in the sensing module. The temperature switch A and the temperature switch B each have two temperature sensing probes 1 and 2, where 1 is to detect the external ambient temperature, and 2 is to detect the human body temperature. For the temperature switch A, when a temperature measured by A1 is greater than or equal to that measured by A2, A is switched off, and when the temperature measured by A1 is less than that measured by A2, A is switched on; for the temperature switch B, when a temperature measured by B1 is less than or equal to that measured by B2, B is switched off, and when the temperature measured by B1 is greater than that measured by B1, B is switched on. A left power supply is connected in series with the temperature switch A, and then connected in parallel with C and R; and a right power supply is connected in series with the temperature switch B, and then connected in parallel with C and R. According to the fact that the vest always needs to be in a working state and with reference to the actual ambient temperature and human body temperature, this circuit is explained in three situations:

(1) When the ambient temperature is greater than the human body temperature, A1 is greater than A2, and the temperature switch A is switched off. B1 is greater than B2, and the temperature switch B is switched on. The thermal-electrical conversion device in the right side works, which supplies energy to various electric devices in the vest on one hand, and stores energy for the electric storage device C on the other hand.

(2) When the ambient temperature is less than the human body temperature, A1 is less than A2, and the temperature switch A is switched on. B1 is less than B2, and the temperature switch B is switched off. The thermal-electrical conversion device in the left side works, which supplies energy to various electric devices in the vest and stores energy for the electric storage device C.

(3) When the ambient temperature is equal to the human body temperature, A1 is equal to A2, and the temperature switch A is switched off. B1 is equal to B2, and the temperature switch B is switched off. Neither the thermal-electrical conversion devices in the left or right side work, and the power storage device C supplies energy to various electric devices in the vest.

A voltage generated by the thermal-electrical conversion may be calculated by using the following formula:

$$U = S(T_h - T_c),$$

where U represents a thermoelectromotive force, S represents a sum of Seebeck coefficients of the two conductors, which is related to the material of the N-type semiconductor and the P-type semiconductor selected, $T_h$ represents a temperature value of the high-temperature heat source, and $T_c$ represents a temperature value of the low-temperature heat source.

A total voltage of the integrated battery is:

$$U_{total} = nU,$$

where n is a quantity of (a) form or (b) form units in the integrated battery device. The difference between the ambient temperature and the human body temperature has little change. Therefore, this embodiment increases the quantity of n as much as possible to increase the total voltage $U_{total}$ of the integrated battery.

Figure 22:
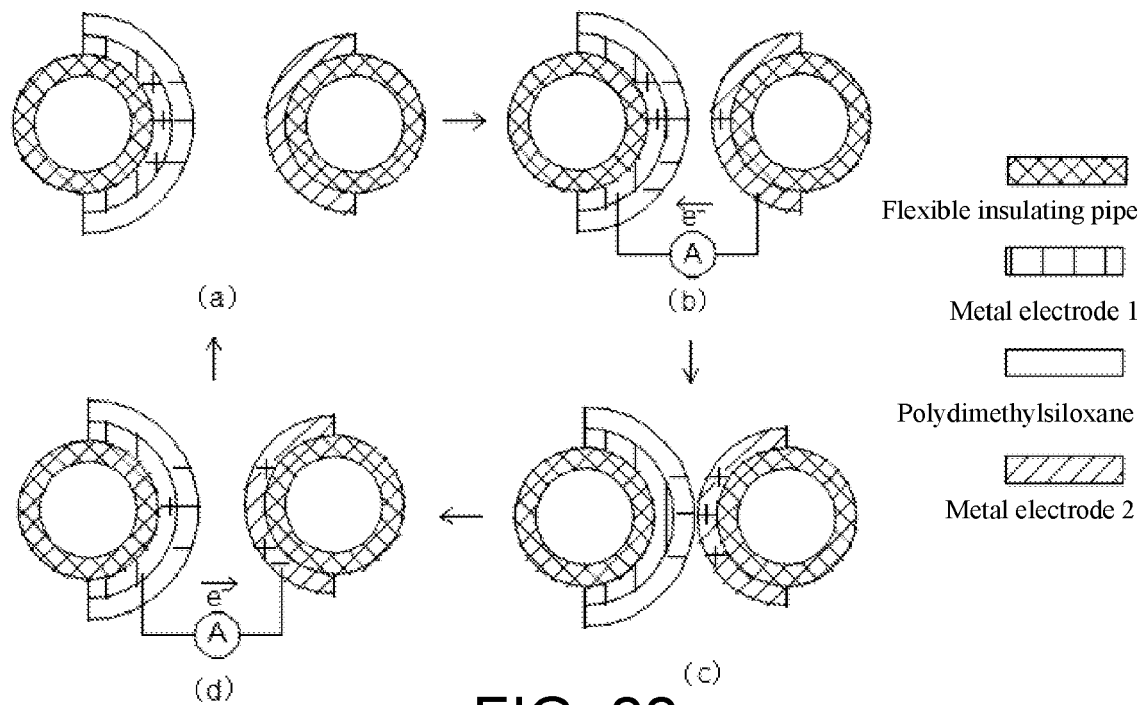
FIG. 22 is a schematic diagram of a principle of dynamic-electrical conversion according to an embodiment of the present invention.

The left battery unit 4-1 and the right battery unit 4-2 may also adopt a dynamic-electrical conversion device to convert biological kinetic energy of the user into electrical energy. The device is mainly composed of a metallic coating on a flexible insulating pipe and a metallic coating on a flexible insulating pipe coated with treated polydimethylsiloxane. The metal coatings on the two flexible insulating pipes are used as two electrodes of the device respectively. Copper and gold with excellent conductivity may be used as the metal. Flexible insulating pipes are made of ethylene-vinyl acetate copolymer, or the like. The treated polydimethylsiloxane makes it easy for polydimethylsiloxane to absorb negative charges to pair that the two flexible insulating pipes. In order to clarify a working mechanism of the flexible insulating pipe, a working process may be simplified, and the two flexible insulating pipes move relatively, so that the metal electrode and the polydimethylsiloxane make a contact separation action. Based on a coupling effect of contact electrification and electrostatic induction, charge movement can be directly generated between the electrodes on the two flexible insulating pipes. The principle is as shown in FIG. 22:

In an original state (a), a surface of the polydimethylsiloxane is filled with negative electrostatic charges, and a metal electrode 1 generates positive charges. When the two flexible insulating pipes are pressed by external kinetic energy, a gap between a metal electrode 2 and the polydimethylsiloxane shrinks due to static induction, which leads to the accumulation of induced positive charges in the metal electrode 2, as shown in (b). Therefore, free electrons in the metal electrode 2 flow to the metal electrode 1 for electric field balance. An instantaneous positive current is produced during this process. It should be noted that the charges on the polydimethylsiloxane will not be destroyed even if the polydimethylsiloxane is contacted with the metal electrode 2, because the electrostatic charges naturally immerse into the insulator polydimethylsiloxane, as shown in (c). In the case that the two flexible insulating pipes are separated again, as shown in (d), the metal electrode 1 and the metal electrode 2 are restored to the original state (1). An instantaneous negative current may be generated. Therefore, during the contact separation process of the two flexible insulating pipes, the kinetic energy is converted into the electrical energy.

Figure 23:
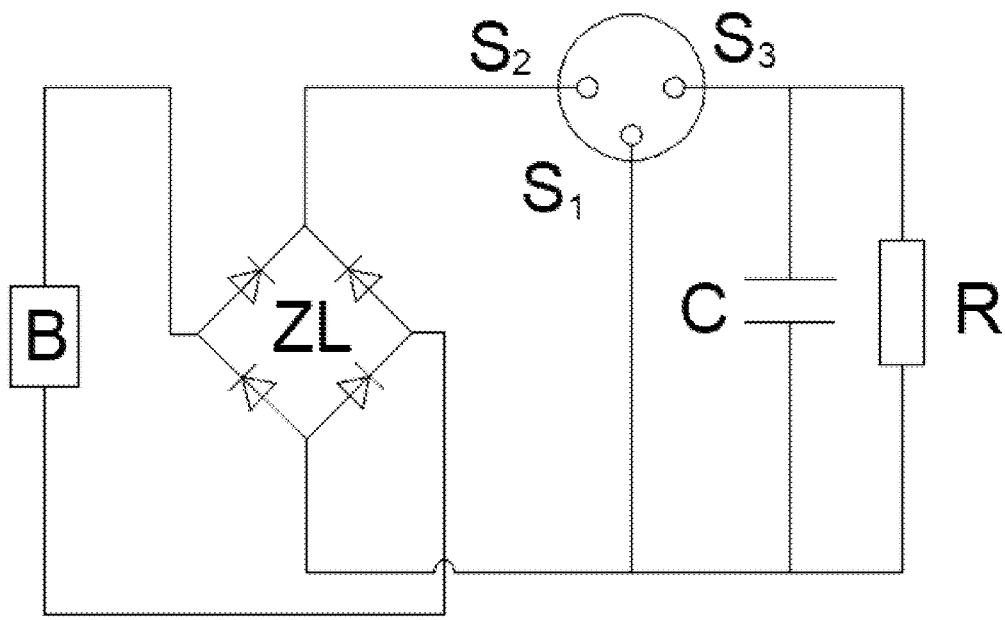
FIG. 23 is a diagram showing that a dynamic-electrical conversion battery module supplies power to a sensing module according to an embodiment of the present invention.

According to the characteristics of the current produced by the dynamic-electrical conversion device and the requirements of this embodiment, a circuit diagram as shown in FIG. 23 is designed. ZL is a rectifier, which aims to convert an alternating current produced by the dynamic-electrical conversion device into a direct current. B is a dynamic-electrical conversion device, C is an energy storing device, which can store electric energy, and R is various power consumption devices in the sensing module. S is a vibration sensing switch. The vibration sensing switch is provided with three switch connectors S1, S2, and S3. When user vibration is sensed by the vibration sensing switch, the switch connector Si is connected to the switch connector S2, and the switch connector S1 is connected to the switch connector S3. When there is no external vibration, the switch connector Si is disconnected from the switch connector S2, and the S1 switch connector is connected to the switch connector S3. According to the fact that this embodiment always needs to be in a working state and with reference to the actual situation of whether the user moves, this circuit is explained in two situations:

(1) When the user moves, the switch connector S1 on the vibration sensing switch is connected to the switch connector S2, and the switch connector S1 is connected to the switch connector S3. At this time, the dynamic-electrical conversion device converts kinetic energy into electrical energy to provide energy for R and stores the electric energy in the energy storage device C.

(2) When the user does not move, the switch connector Si on the vibration sensing switch is disconnected from the switch connector S2, and the switch connector Si is connected to the switch connector S3. At this time, the energy storing device C works to release the electrical energy stored therein to provide energy for R.

Figure 24:
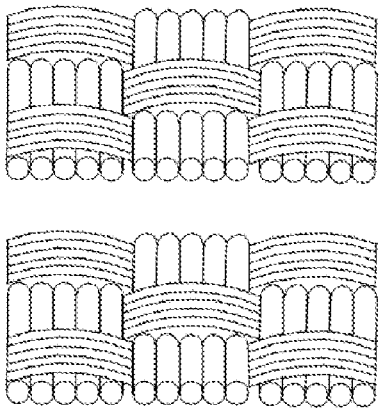
FIG. 24 is a structural form diagram of the dynamic-electrical conversion battery module according to an embodiment of the present invention.

A structural form of the dynamic-electrical conversion device is as shown in FIG. 24. The flexible insulating pipe with the metal coating only is woven as one surface, and the flexible insulating pipe with metal coating covered by polydimethylsiloxane is woven as another surface. In view of that further expanding the contact between the two surfaces is beneficial for static induction, a knitting pattern is 5×5. The knitting pattern is sewed on the carrier of the embodiment.

A photovoltaic power storage in-situ integrated battery based on optical-electrical conversion is used in the wristband battery device 7-1 and the headband battery device 10-1. The photovoltaic power storage in-situ integrated battery is mainly prepared by assembling a photovoltaic conversion functional film component and an electric storage functional film component layer by layer in situ, which sequentially includes a base layer/electrode, a photovoltaic battery part, a transition electrode, an energy storage part, and a base layer/electrode from top to bottom. The photovoltaic battery part may adopt:

(1) a silicon-based solar battery composed of a P-N junction formed by a silicon substrate doped with an n-type or p-type semiconductor; in the presence of sunlight illumination, the silicon substrate produces a photoelectric effect, and when the two ends are connected into a circuit, a current is produced;

(2) a sensitized solar battery composed of a conductive substrate, a semiconductor nano-porous film, a dye sensitizer, an electrolyte containing a redox couple, and a counter electrode; in the presence of sunlight illumination, dye molecules are excited from a ground state to an excited state, and electrons are injected into the semiconductor nano-porous film, the electrons may be quickly enriched on the conductive substrate, and flow to the counter electrode through an external conductor; and (3) a formal perovskite solar battery composed of a conductive layer, an electron transport layer, a perovskite light-absorption layer, a hole transport layer, and an electrode, and a trans-perovskite solar battery composed of a conductive layer, a hole transport layer, a perovskite light-absorption layer, an electron transport layer, and an electrode. In the presence of sunlight illumination, a large quantity of electron-hole pairs may be generated in the perovskite light-absorption layer, where electrons and holes are respectively collected by the electron transport layer and the hole transport layer and transmitted to the electrode. When the two ends are connected into a circuit, a current may be generated.

A performance of the photovoltaic battery part may be calculated by the following formula:

$$E_{solar} = P_{in} \cdot A_{solar} \cdot t,$$

where $E_{solar}$ is a photoelectric conversion power, t is a sunlight irradiation time, $A_{solar}$ is a light-absorption area of the photovoltaic battery part, and $P_{in}$ is an incident light power density, where an international standard is 100 mW/cm$^2$. The sunlight irradiation time depends on a plurality of factors, such as weather, outdoor time of the user, and the like. To improve the performance of the photovoltaic battery part, in this embodiment, the light-absorption area of the photovoltaic battery part is increased as much as possible.

A capacitor or a lithium battery may be used as the energy storage part for storing electric energy. A metal with a good conductivity may be used as the electrode.

Figure 25:
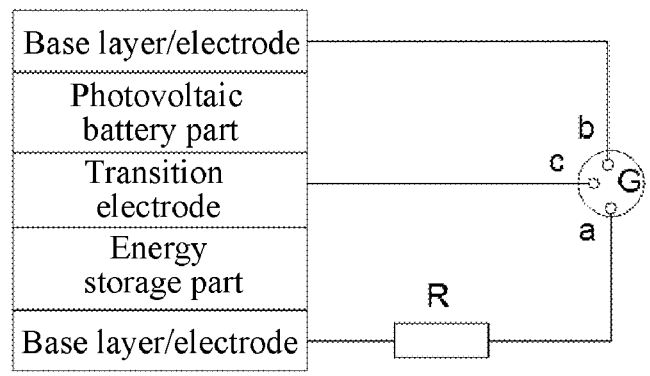
FIG. 25 is a diagram showing that an optical-electrical conversion battery module supplies power to a sensing module according to an embodiment of the present invention.

In this embodiment, a circuit as shown in FIG. 25 is designed considering that this embodiment is always working regardless of the existence of sunshine in the external environment. R refers to various electrical devices in the sensing module, and G refers to a light sensing switch. The light sensing switch is provided with three switch connectors a, b, and c. The switch connector a is connected to the switch connector c when there is light outside, and the switch connector a is connected to the switch connector b when there is no light outside. a is connected in series with R through a wireway, and R is connected to a base layer/electrode through a wireway. b is connected in series with a transition electrode through a wireway, and c is connected to the base layer/electrode through a wireway. According to the variable of sunlight, this circuit is explained in two situations:

(1) when there is sunlight in the daytime, the switch connector a on the light sensing switch is connected to the switch connector c. At this time, the photovoltaic battery part works, which converts light energy into electrical energy to provide energy for R, and stores the electric energy in the energy storage device C.

(2) when there is no sunlight at night, the switch connector a on the light sensing switch is connected to the switch connector b. At this time, the energy storage part works to release the electrical energy stored therein to provide energy for R.

Figure 26:
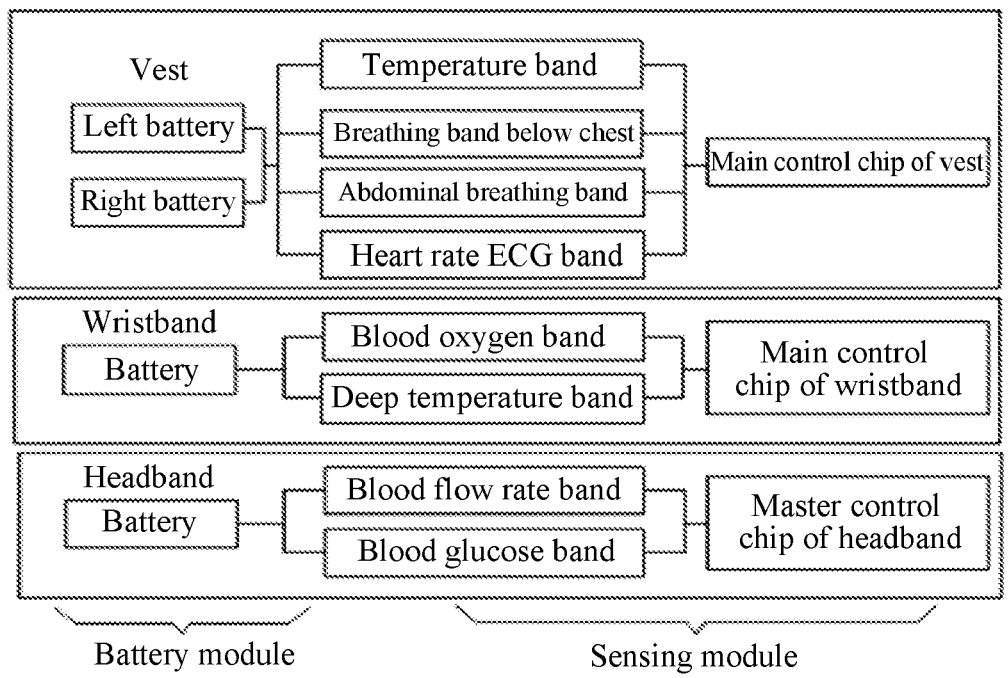
FIG. 26 is a frame diagram of an information collection module according to an embodiment of the present invention.

Conductor connection of a signal collection module is explained with FIG. 26. For the vest, conductors are arranged inside the vest left front piece 2-2, the right front piece 2-3 and the vest back piece 2-1. The shell temperature band 3-1, the chest breathing band 3-2, the abdominal breathing band 3-3, the heart rate ECG band 3-4, and the vest main control chip 2-15 are connected by the conductors to transmit physical sign parameter signals of the user measured by the shell temperature band 3-1, the chest breathing band 3-2, the abdominal breathing band 3-3, and the heart rate ECG band 3-4 to the vest main control chip 2-15. The left battery device 4-1 and the right battery device 4-2 are connected to the transformer through conductors to change the voltages, and then, respectively connected to the shell temperature band 3-1, the chest breathing band 3-2, the abdominal breathing band 3-3, the heart rate ECG band 3-4, and the vest main control chip 2-15 through the conductors to convey electric energy.

For the wristband, the wristband body 5-1 is internally provided with conductors. The blood flow rate band 6-1, the blood glucose band 6-2, and the wristband main control chip 5-3 are connected by the connectors to transmit physical sign parameter signals of the user measured by the blood flow rate band 6-1 and the blood glucose band 6-2 to the wristband main control chip 5-3. The wristband battery device 7-1 is connected to the transformer through a wireway to change the voltages, and then, respectively connected to the blood flow rate band 6-1, the blood glucose band 6-2, and the wristband main control chip 5-3 through the conductors to convey electric energy.

For the headband, the headband body 8-1 is internally provided with conductors. The blood oxygen band 9-1, the deep temperature band 9-2 and the headband main control chip 8-3 are connected by the connectors to transmit physical sign parameter signals of the user measured by the blood oxygen band 9-1 and the deep temperature band 9-2 to the headband main control chip 8-3. The headband battery device 10-1 is connected to the transformer through a wireway to change the voltages, and then respectively connected to the blood oxygen band 9-1, the deep temperature band 9-2 and the headband main control chip 8-3 through the conductors to convey electric energy.

Information transmission and information processing and feedback modules include mobile phone terminals, various databases and institutional facilities. As one of the necessary communication tools in modern life, the mobile phone has very powerful functions in processing, storing and transmitting data. In this embodiment, the mobile phone terminal serves as a transfer station for storing and sending data, and also analyzes and processes the stored data and gives an alarm for abnormal data. The various databases and institutional facilities include large databases, sub-health and disease databases, disease control centers, pharmaceutical institutions and hospital institutions. The various databases and institutional facilities are used for receiving the data about physical sign parameters, personal information and geographical location of the user sent by the mobile phone, and analyzing and processing the received physical sign parameters of the user step by step. Through analysis and processing, a health status of the user is sent to the mobile phone terminal in a form to give the user feedback. In addition, the alarm of the mobile phone terminal is handled urgently.

The vest main control chip 2-15, the wristband main control chip 5-3 and the headband main control chip 7-3 in the information collection module are used for collecting and storing the data transmitted by the shell temperature band 3-1, the chest breathing band 3-2, the abdominal breathing band 3-3, the heart rate ECG band 3-4, the blood flow rate band 6-1, the blood glucose band 6-2, the blood oxygen band 9-1 and the deep temperature band 9-2, and transmitting the collected information about the physical sign parameters of the user to the mobile phone via Bluetooth® for subsequent analysis and feedback process.

Figure 27:
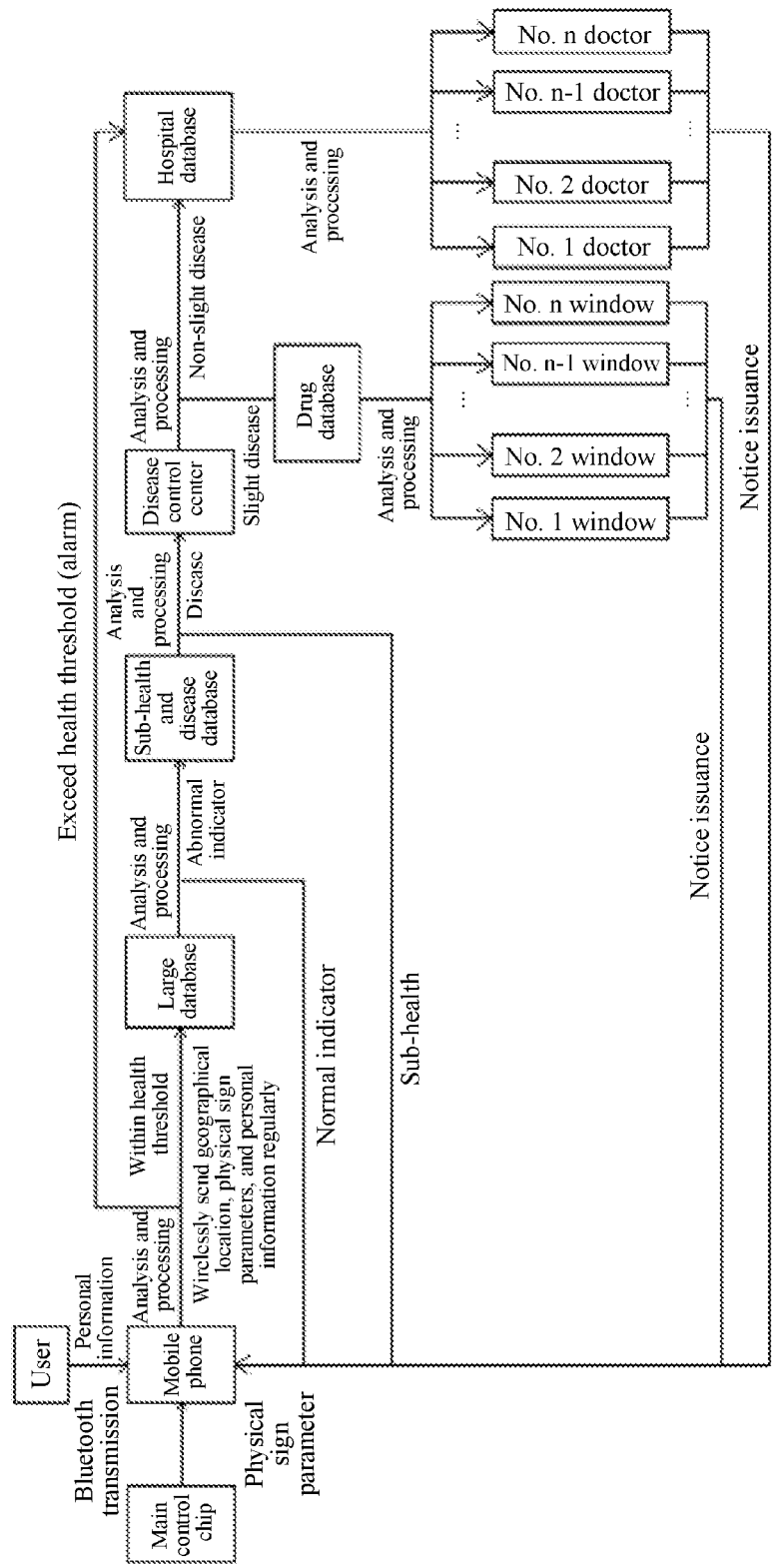
FIG. 27 is a frame diagram of an information transmission, information processing and feedback module according to an embodiment of the present invention.

The framework of information transmission, information processing and feedback is as shown in FIG. 27. The collected personal information and physical sign parameters of the user may be analyzed and processed in five levels in the whole transmission process, a report is generated from results and sent to the mobile phone for feedback, and the user is arranged for relevant treatment according to the results. The whole process is established based on the internet. The whole process is described hereinafter according to FIG. 27.

The user enters personal information (such as a gender, a race, an age, and the like) into the mobile phone first, and the master control chip may continuously transmit the collected information about the physical sign parameters of the user to the mobile phone via Bluetooth®. A preset health threshold of people is set in advance in the mobile phone, and the mobile phone may analyze and process the collected information in a first level. If the collected information does not exceed the preset health threshold of people, the collected information may be sorted out by the mobile phone, and wirelessly transmitted to the large database on a daily basis regularly, and the sorted physical sign parameters, personal information, and geographical location of one day are wirelessly transmitted to the large database. If the physical sign parameters of the received user exceed the preset health threshold set in advance, the mobile phone may give an alarm immediately. The mobile phone may wirelessly transmit abnormal physical sign data, personal information, and geographical location of the user to the hospital database immediately and inform the user that emergency treatment is needed. The hospital database may select a nearby hospital according to the geographical location of the user and transmit the abnormal physical sign data and the personal information of the user to the hospital, and the hospital may provide emergency medical treatment for the user.

The large database may analyze and process the physical sign parameters, the personal information, and the geographical location of the user transmitted from the mobile phone in a second level, the received information is compared through the existing physical sign parameters, gender, race, and age of people in the large database, and the received information is divided into abnormal indicators and normal indicators, which are processed separately. For the normal indicators, a health state of the user at the moment is sent to the mobile phone in a form of report. For the abnormal indicators, the data information, personal information, and geographical location are sent to a sub-health and disease database by wireless transmission for analysis and processing in a third level.

The collected data information of abnormal indicators is analyzed and processed by the sub-health and disease database, and compared with existing data of the sub-health and disease database. The data information of abnormal indicators is divided into sub-health information and disease information, a targeted response is made to the sub-health information, feedback is given to the mobile phone, a report is generated to inform the user of a current health state, and a solution to the sub-health state is given at the moment. For the disease information, the disease information, the personal information, and the geographical location may be sent to the sub-health and disease database by wireless transmission for analysis and processing in a fourth level.

A disease control center analyzes and processes received disease data information. Firstly, a region where the user is located is determined according to mobile phone location of the user, and secondly, diseases caused by the data information of the abnormal indicators are divided into a slight disease and a non-slight disease. For the slight disease, the data information is sent to a drug institution closest to the user for analysis and processing in the third level. For the non-slight disease, the data information is sent to a hospital institution closest to the user for analysis and processing in a fifth level.

A drug organization may analyze and process the collected information through a drug database, allocate required drug measurements according to various slight diseases, link various slight diseases with drug windows corresponding to the various slight diseases, and send the drug measurements to the drug windows. The drug window may select a drug according to the drug measurement first, then send the health state of the user at the moment to the mobile phone in a form of a report, and inform the user to take the drug from the drug window corresponding to the slight disease suffered by the user.

A hospital institution may classify the non-slight diseases through specific analysis and determination of the hospital database, send the non-slight diseases to departments related to the diseases, and inform relevant professional doctors to issue a notice for the user to come for treatment.

In this embodiment, a Bluetooth® transmission technology and a wireless transmission technology are mature and can be used directly.

The specific implementations of the present invention are described above with reference to the accompanying drawings, but are not intended to limit the protection scope of the present invention. Those skilled in the art should understand that various modifications or deformations may be made without creative efforts based on the technical solutions of the present invention, and such modifications or deformations shall fall within the protection scope of the present invention.

What is claimed is:

1. A flexible sensor detection system for medical care and health, comprising:
    a wearable device, consisting of a wearable vest, a wristband, and a headband, wherein the headband has a band head and a band tail being connected to each other through an adjustable button;
    the wearable device having arranged thereon, a plurality of flexible sensors, said flexible sensors configured to collect a heart rate parameter, an electrocardiogram (ECG) parameter, a breathing parameter, a temperature parameter, a bloodflow rate parameter, a blood glucose parameter, and a blood oxygen parameter of a user of the wearable device in real time;
    a mobile phone terminal, configured to wirelessly transmit the heart rate parameter, the ECG parameter, the breathing parameter, the temperature parameter, the blood flow rate parameter, the blood glucose parameter, and the blood oxygen parameter which are collected to a plurality of databases and institutional facilities;
    the plurality of databases and institutional facilities, configured to analyze and process the heart rate parameter, the ECG parameter, the breathing parameter, the temperature parameter, the blood flow rate parameter, the blood glucose parameter, and the blood oxygen parameter transmitted from the mobile phone terminal in a manner of the user being arranged for relevant treatment according to results of the analyzing and processing and generating a report containing the relevant treatment according to the results of the analyzing and processing; and
    a battery comprising a dynamic-electrical conversion device to convert biological kinetic energy of the user into electrical energy, comprising a first flexible insulating pipe with a first metal coating on a periphery thereof and a second flexible insulating pipe with a second metal coating on a periphery thereof and a polydimethylsiloxane cover on the periphery of the second metal coating; wherein, the first flexible insulating pipe is woven as one surface, and the second flexible insulating pipe is woven as another surface, to form a knitting pattern with a size of 5strands x5strands, and the knitting pattern is sewed on the wearable vest;
    wherein, the wearable vest comprises a vest back piece, a vest left front piece, and a vest right front piece; the battery comprises a left battery unit and a first temperature switch being provided on the vest left front piece, a right battery unit and a second temperature switch being provided on the vest right front piece, and a capacitor or a lithium battery, used as a power storage unit, being provided on the vest back piece.

2. The flexible sensor detection system for medical care and health according to claim 1, wherein the flexible sensors at least comprise: a flexible heart rate sensor and a flexible breathing sensor, wherein:
    the flexible heart rate sensor or the flexible breathing sensor comprises: an encapsulation layer based on piezoelectric effect, an upper electrode of a flexible piezoelectric film, the flexible piezoelectric film, a lower electrode of the flexible piezoelectric film, and a base layer based on piezoelectric effect which are sequentially arranged from top to bottom; wherein, the upper electrode of the flexible piezoelectric film, the flexible piezoelectric film, and the lower electrode of the flexible piezoelectric film constitute a functional layer; when the functional layer is excited by a heart beating or breathing movement of a user, the flexible piezoelectric film bends, and piezoelectric charges are generated at the moment of bending, which accumulate at both ends of the upper and lower electrodes to generate a potential difference, thereby converting a heart rate and breathing signal into an electrical signal.

3. The flexible sensor detection system for medical care and health according to claim 1, wherein
    an inner side face of a front chest in the vest right front piece is provided with a heart rate ECG band for collecting the heart rate parameter and the ECG parameter of a wearer; a breathing band is arranged on an abdomen inside the vest left front piece, the right front piece, and the vest back piece, which surrounds a body by one circle for collecting the breathing parameter, and a shell temperature band is arranged at an armpit inside the vest left front piece for collecting a shell temperature parameter; an outer side face of the vest right front piece is provided with a first master control chip configured for storing the heart rate parameter, the ECG parameter, the breathing parameter, and the shell temperature parameter; and the heart rate ECG band, the breathing band, and the shell temperature band are respectively connected to the first master control chip.

4. The flexible sensor detection system for medical care and health according to claim 3, wherein the vest left front piece is connected to the vest back piece through a left shoulder band, the vest right front piece is connected to the back piece of the vest through a right shoulder band, and first adjustable buttons are arranged at the left and right shoulder bands of the vest, a second adjustable button is arranged at a boundary between the vest left front piece and a left side of the vest back piece, a third adjustable button is arranged at a boundary between the vest right front piece and a right side of the vest back piece, a front end of the vest is provided with an opening zipper, and the left front piece and the right front piece of the vest are provided with connector interfaces of the breathing band.

5. The flexible sensor detection system for medical care and health according to claim 1, wherein an inner side of the wristband is provided with a blood flow rate band for collecting the blood flow rate parameter; the inner side of the wristband is provided with a blood glucose band for collecting the blood glucose parameter; an outer side face of a wristband body is provided with a second master control chip configured for storing the blood flow rate parameter and the blood glucose parameter; and the blood flow rate band and the blood glucose band are respectively connected to the second master control chip.

6. The flexible sensor detection system for medical care and health according to claim 1, wherein an inner side of the headband is provided with a blood oxygen band for collecting the blood oxygen parameter, the headband is provided with a deep temperature band for collecting a deep temperature parameter; an outer side face of the headband is provided with a third master control chip configured for storing the blood oxygen parameter and the deep temperature parameter; and the blood oxygen band and the deep temperature band are respectively connected to the third master control chip.

7. The flexible sensor detection system for medical care and health according to claim 1, wherein the battery further adopts a principle of thermal-electrical conversion, comprising a loop formed by a P-type semiconductor and an N-type semiconductor, wherein in a presence of an external load, if temperatures at two end faces of the P-type semiconductor and the N-type semiconductor are different, then a voltage and a current is generated in the loop, wherein the P-type semiconductor is an anode of the battery and the N-type semiconductor is a cathode of the battery; wherein, the first temperature switch has two temperature sensing probes A1 and A2, and the second temperature switch has two temperature sensing probes B1 and B2, wherein the temperature sensing probes A1 and B1 are configured to detect an external ambient temperature, and the temperature sensing probes A2 and B2 are configured to detect a human body temperature, wherein, the left battery unit is connected in series with the first temperature switch, and then connected in parallel with the power storage unit and the flexible sensors; and the battery unit is connected in series with the second temperature switch, and then connected in parallel with the power storage unit and the flexible sensors; according to a fact that the wearable vest always needs to be in a working state and with reference to an actual ambient temperature and human body temperature, the loop is in three situations:

(1) when the ambient temperature is greater than the human body temperature, a measured value of the temperature sensing probe A1 is greater than that of the temperature sensing probe A2, and the first temperature switch is switched off; a measured value of the temperature sensing probe B1 is greater than that of the temperature sensing probe B2, and the second temperature switch is switched on, the right battery unit works, supply energy to the flexible sensors, and to the power storage device for storing simultaneously;

(2) when the ambient temperature is less than the human body temperature, the measured value of the temperature sensing probe A1 is less than that of the temperature sensing probe A2, and the first temperature switch is switched on; the measured value of the temperature sensing probe B1 is less than the temperature sensing probe B2, and the second temperature switch is switched off, the left battery unit works, supply energyto the flexible sensors, and to the power storage device for storing simultaneously;

(3) when the ambient temperature is equal to the human body temperature, the measured value of the temperature sensing probe A1 is equal to that of the temperature sensing probe A2, and the first temperature switch is switched off; the measured value of the temperature sensing probe B1 is equal to that of the temperature sensing probe B2, and the second temperature switch is switched off, neither the left battery unit or the right battery unit works, and the power storage unit supplies energy to the flexible sensors in the wearable vest.

* * * * *

UNITED STATES PATENT AND TRADEMARK OFFICE
CERTIFICATE OF CORRECTION

| | |
|---|---|
| PATENT NO. | : 12,245,871 B2 |
| APPLICATION NO. | : 17/281998 |
| DATED | : March 11, 2025 |
| INVENTOR(S) | : Changhe Li et al. |

Page 1 of 1

It is certified that error appears in the above-identified patent and that said Letters Patent is hereby corrected as shown below:

On the Title Page

Item (73) Assignees should read:
QINGDAO UNIVERSITY OF TECHNOLOGY, Shandong (CN);
QINGDAO HUANGHAI UNIVERSITY, Shandong (CN);
GUOHUA (QINGDAO) INTELLIGENT PRECISION DRIVE CONTROL TECHNOLOGY RESEARCH INSTITUTE CO., LTD., Shandong (CN);
QINGDAO JIMO QINGLI INTELLIGENT MANUFACTURING INDUSTRY RESEARCH INSTITUTE, Shandong (CN)

Signed and Sealed this
Third Day of June, 2025

Coke Morgan Stewart
*Acting Director of the United States Patent and Trademark Office*